United States Patent
Baumann et al.

(10) Patent No.: US 9,490,431 B2
(45) Date of Patent: Nov. 8, 2016

(54) COPPER(I) COMPLEXES, IN PARTICULAR FOR OPTOELECTRONIC COMPONENTS

(75) Inventors: Thomas Baumann, Karlsruhe (DE); Tobias Grab, Karlsruhe (DE); Daniel Zink, Karlsruhe (DE)

(73) Assignee: CYNORA GMBH, Bruchsal (DE)

( * ) Notice: Subject to any disclaimer, the term of this patent is extended or adjusted under 35 U.S.C. 154(b) by 512 days.

(21) Appl. No.: 14/117,190

(22) PCT Filed: May 14, 2012

(86) PCT No.: PCT/EP2012/058957
§ 371 (c)(1),
(2), (4) Date: Mar. 6, 2014

(87) PCT Pub. No.: WO2012/156378
PCT Pub. Date: Nov. 22, 2012

(65) Prior Publication Data
US 2014/0166944 A1     Jun. 19, 2014

(30) Foreign Application Priority Data

| May 13, 2011 | (EP) | .................................... | 11166075 |
| Jul. 8, 2011 | (EP) | .................................... | 11173369 |
| Aug. 26, 2011 | (EP) | .................................... | 11179110 |

(51) Int. Cl.
*H01L 51/00* (2006.01)
*C07F 9/58* (2006.01)
(Continued)

(52) U.S. Cl.
CPC ........... *H01L 51/0003* (2013.01); *C07F 9/587* (2013.01); *C07F 9/65066* (2013.01);
(Continued)

(58) Field of Classification Search
None
See application file for complete search history.

(56) References Cited

U.S. PATENT DOCUMENTS

| 2010/0252820 A1* | 10/2010 | De Cola | .............. C07D 401/04 257/40 |
| 2011/0284799 A1* | 11/2011 | Stoessel | .................... C07F 1/00 252/301.16 |

FOREIGN PATENT DOCUMENTS

| JP | 2005089367 A | 4/2005 |
| JP | 2012530762 A | 12/2012 |

(Continued)

OTHER PUBLICATIONS

Zhou et al., "Di-μ3-bromo-dibromotetrakis[μ-diphenyl-(2-pyridyl)phosphine)]tetracopper(1) dichloromethane hexasolvate," Acta Crystallographica, Section E: Structure Reports Online, 2003, V59, N4, pp. m176-m178.

*Primary Examiner* — Nathan T Leong
(74) *Attorney, Agent, or Firm* — Ryan, Mason & Lewis, LLP

(57) ABSTRACT

The invention relates to copper(I) complexes of the formula A,

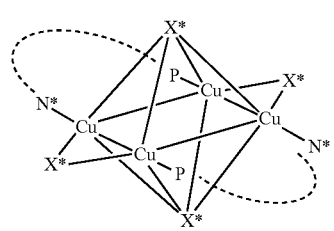

Formula A in which
X*=Cl, Br, I, CN and/or SCN (i.e. independently of one another);
N*∩E=a bidentate ligand where
  E=phosphanyl/arsenyl group of the $R_2E$ form (where R=alkyl, aryl, alkoxyl, phenoxyl, or amide);
  N*=imine function, which is part of a N-heteroaromatic 5- or 6-membered ring, which is chosen from the group consisting of oxazole, imidazole, thiazole, isoxazole, isothiazole, pyrazole, 1,2,3-triazole, 1,2,3-oxadiazole, 1,2,5-oxadiazole, 1,2,3-thiadiazole and 1,2,5-thiadiazole, pyridine, pyrimidine, triazine, pyrazine and pyridazine; and
  "∩"=at least one carbon atom, which is likewise part of the aromatic group, wherein the carbon atom is directly adjacent to both the imine nitrogen atom and to the phosphorous or arsenic atom.

16 Claims, 20 Drawing Sheets

Crystal structure of 2b:

(51) Int. Cl.
| | |
|---|---|
| *C07F 9/6506* | (2006.01) |
| *C07F 9/6512* | (2006.01) |
| *C07F 9/6518* | (2006.01) |
| *C07F 9/653* | (2006.01) |
| *C07F 9/6539* | (2006.01) |
| *H01L 51/50* | (2006.01) |

(52) U.S. Cl.
CPC ....... *C07F9/65068* (2013.01); *C07F 9/65126* (2013.01); *C07F 9/65186* (2013.01); *C07F 9/65318* (2013.01); *C07F 9/65324* (2013.01); *C07F 9/65397* (2013.01); *H01L 51/0008* (2013.01); *H01L 51/009* (2013.01); *H01L 51/0091* (2013.01); *H01L 51/5016* (2013.01); *Y02E 10/549* (2013.01)

(56) References Cited

FOREIGN PATENT DOCUMENTS

| | | |
|---|---|---|
| JP | 2014527030 A | 10/2014 |
| JP | 2014532034 A | 12/2014 |
| WO | 2010/149748 A1 | 12/2010 |
| WO | WO2010149748 * | 12/2010 |

* cited by examiner

Figure 1: Crystal structure of 2b:
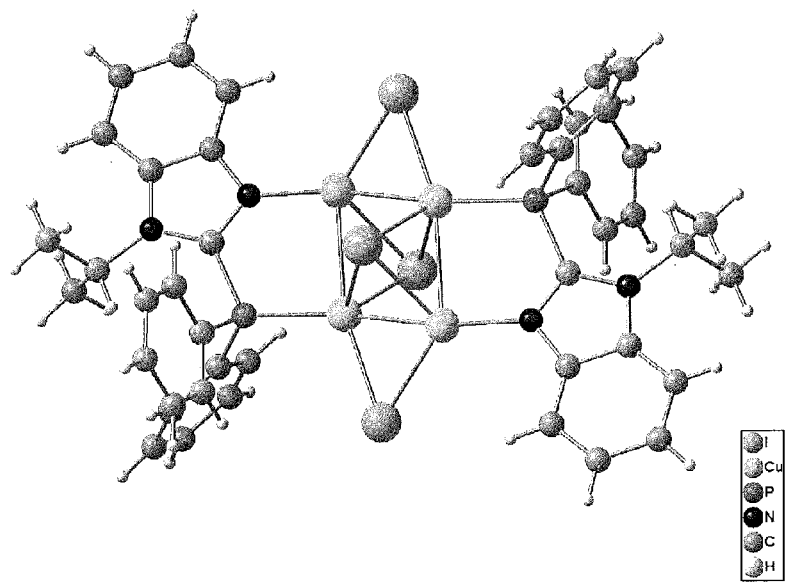
Figure 2: Crystal structure of 2c:
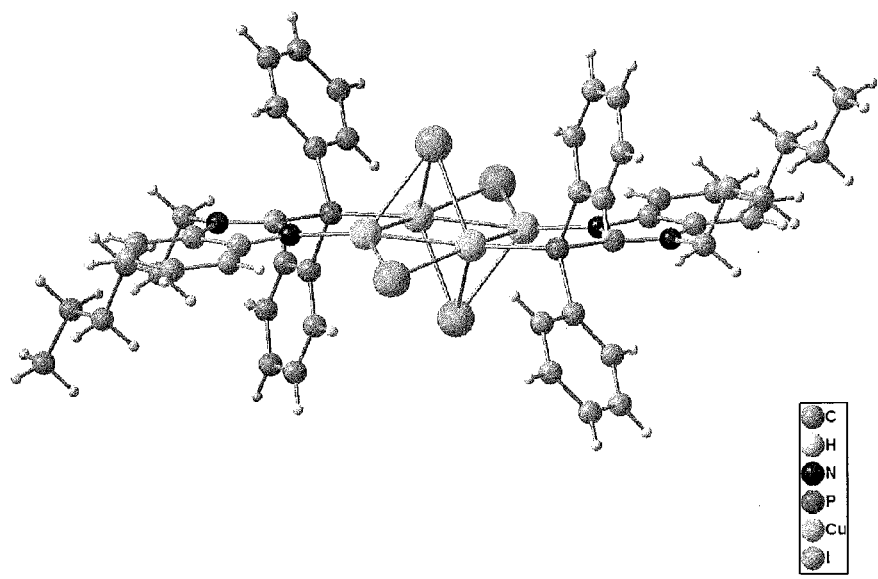

Figure 3: Crystal structure of 2e:
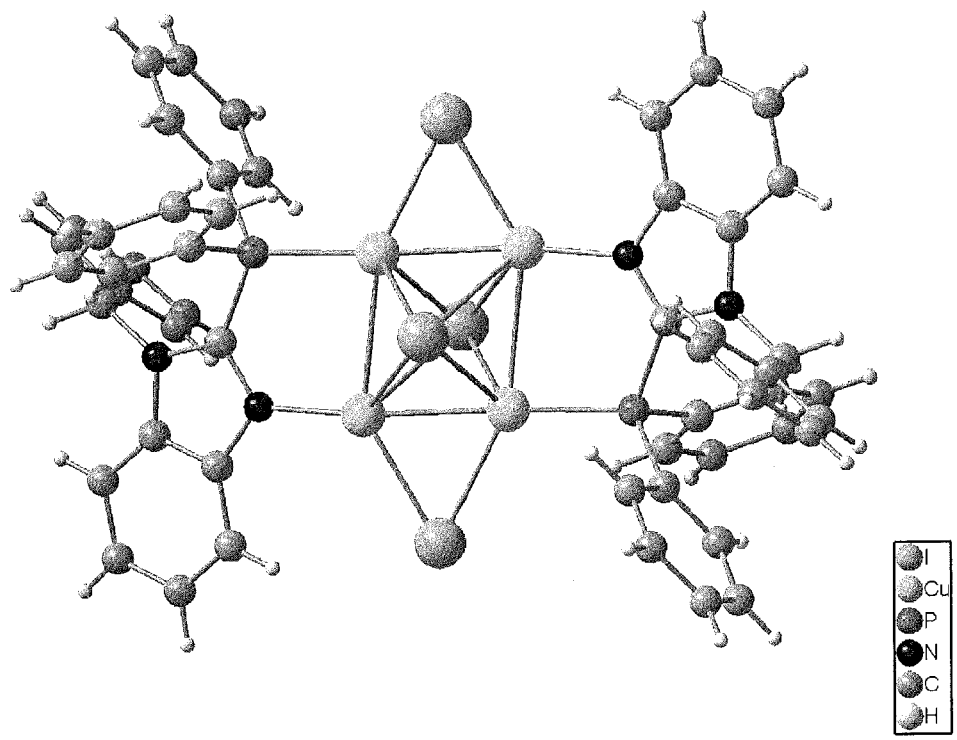
Figure 4: Emission spectrum of 2a:
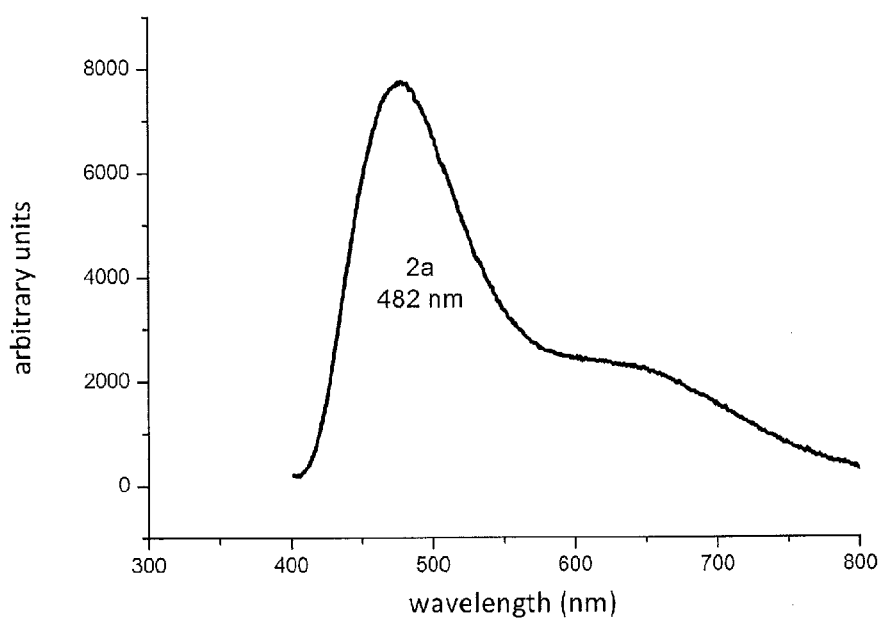

Figure 5: Emission spectrum of 2b:
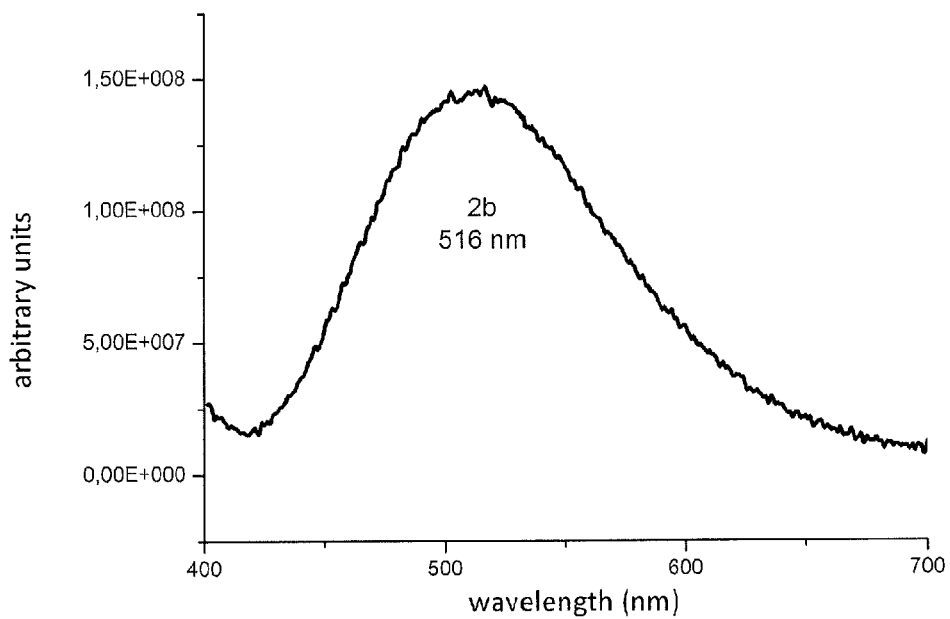
Figure 6: Emission spectrum of 2c:
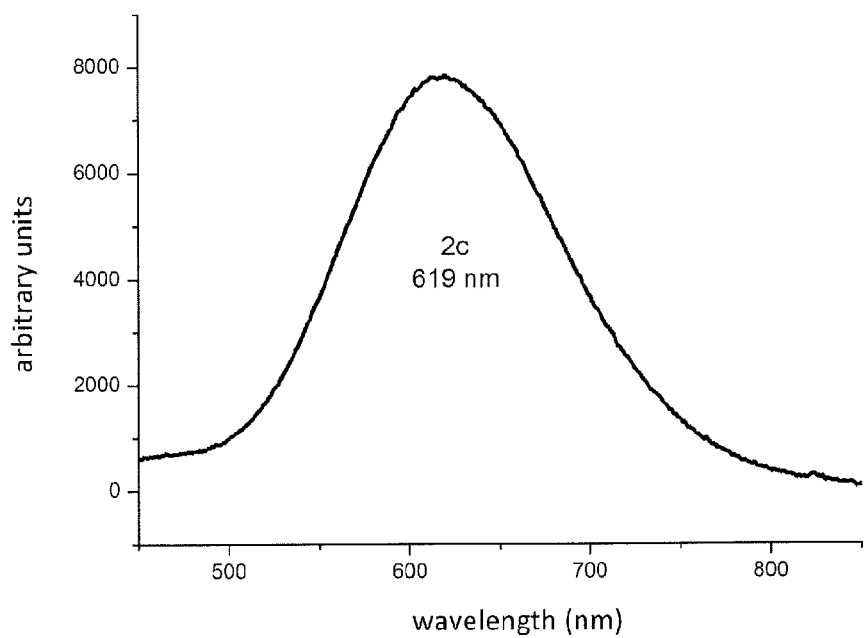

Figure 7: Emission spectrum of 2c:
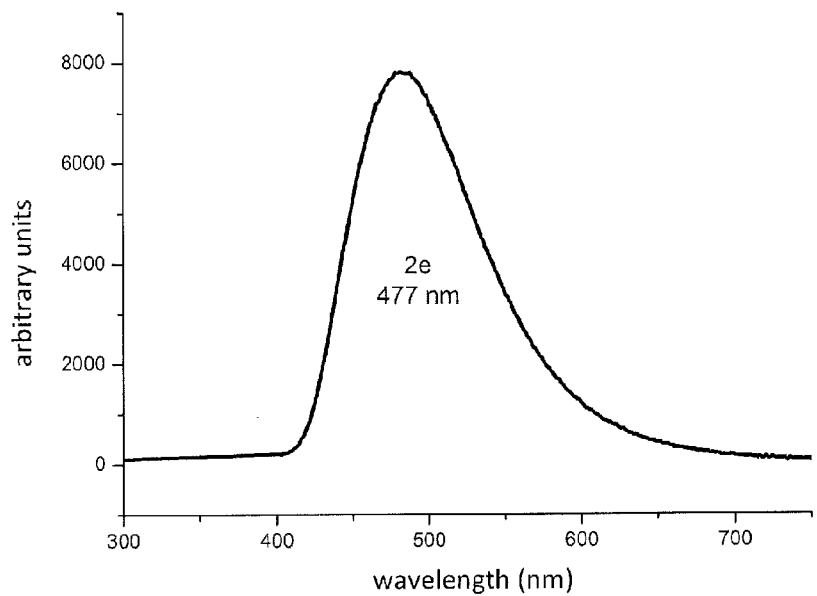
Figure 8: Crystal structure of 4c:
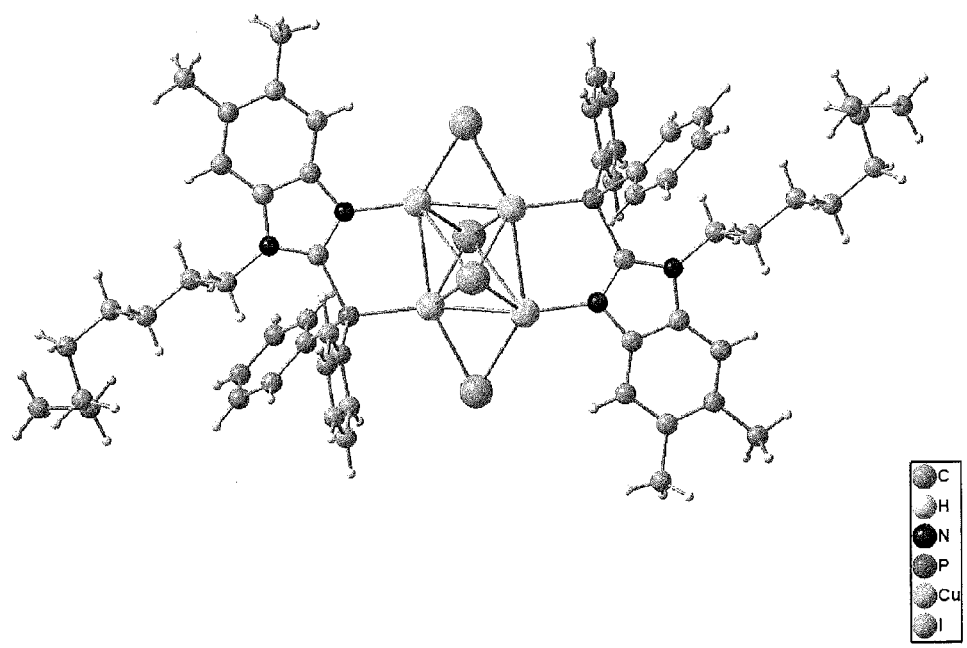

Figure 9: Crystal structure of 4d:
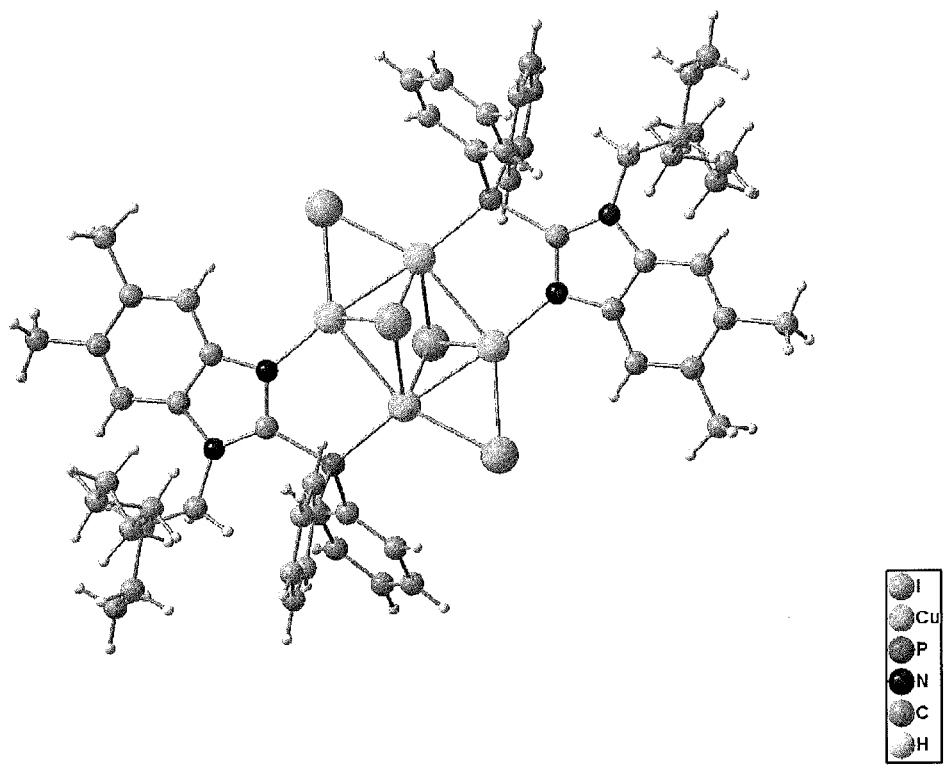
Figure 10: Crystal structure of 4e:
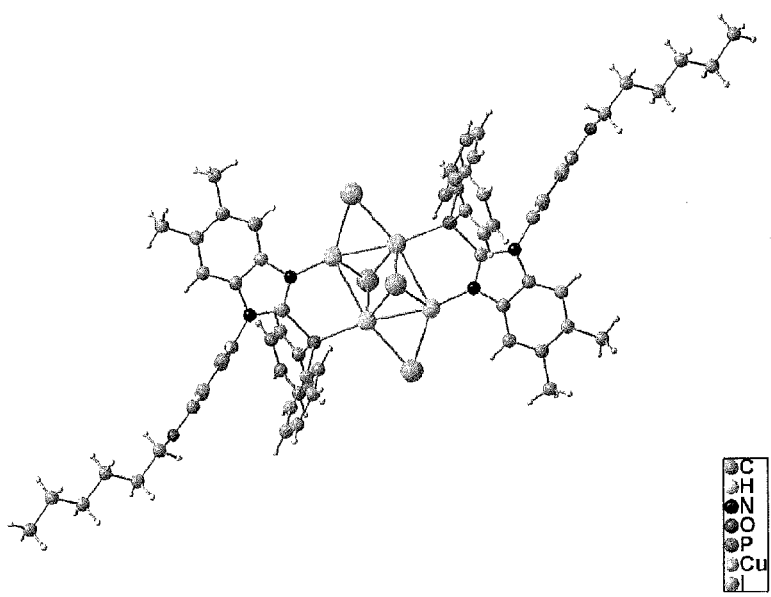

Figure 11: Emission spectrum of 4a:
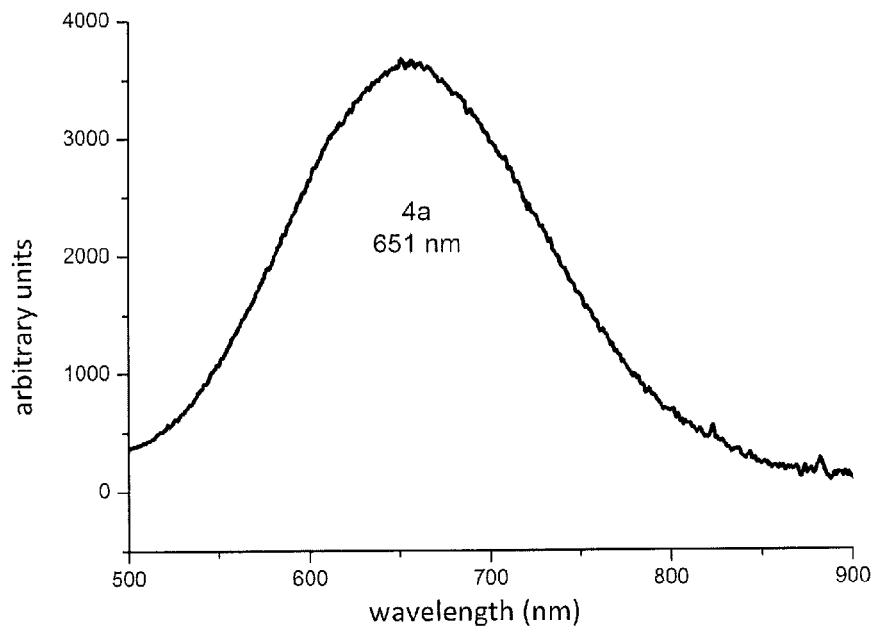
Figure 12: Emission spectrum of 4c:
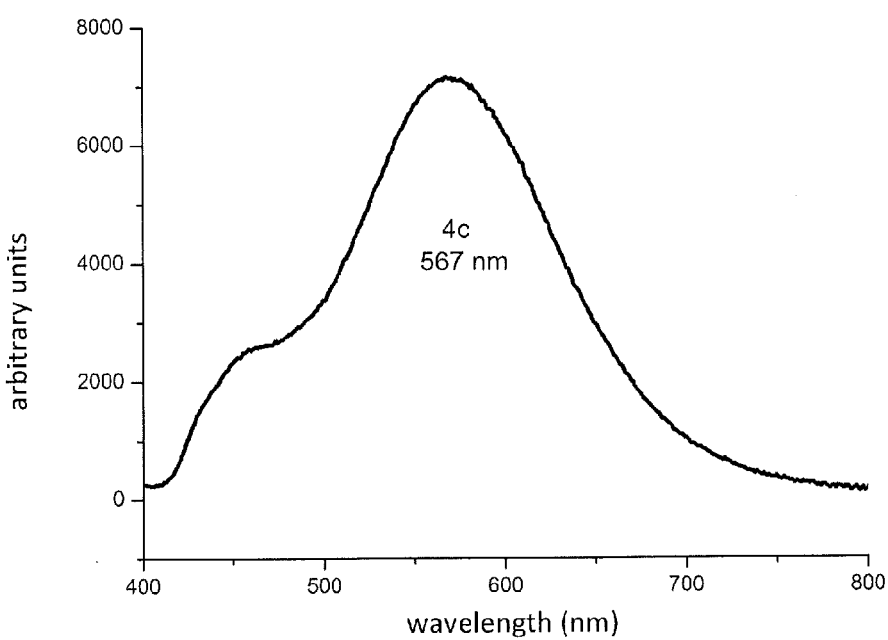

Figure 13: Emission spectrum of 4d:
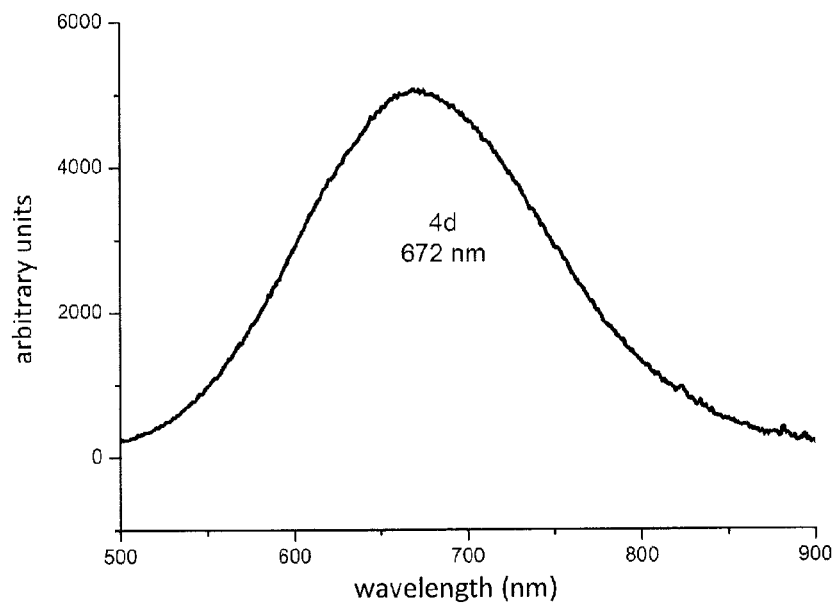
Figure 14: Emission spectrum of 4f:
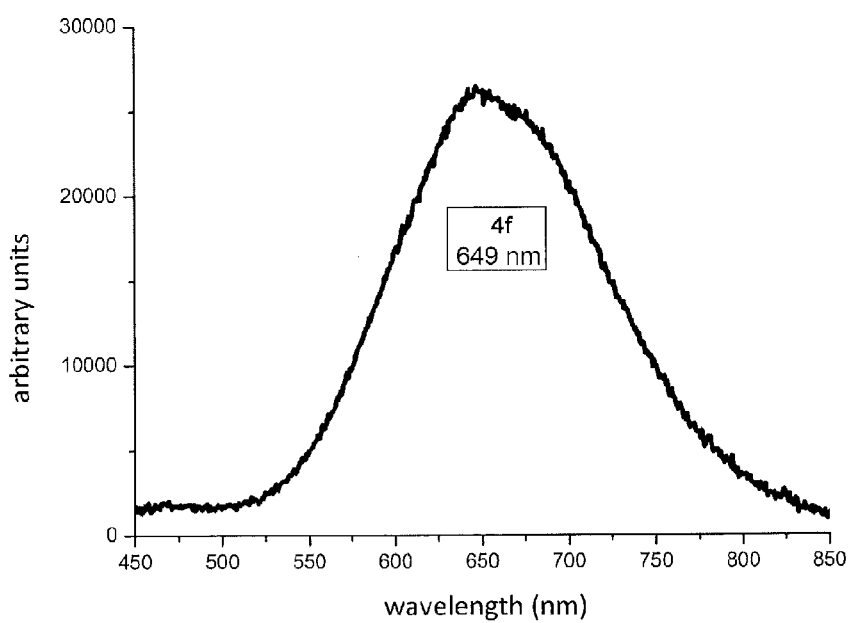

Figure 15: Emission spectrum of 4g:
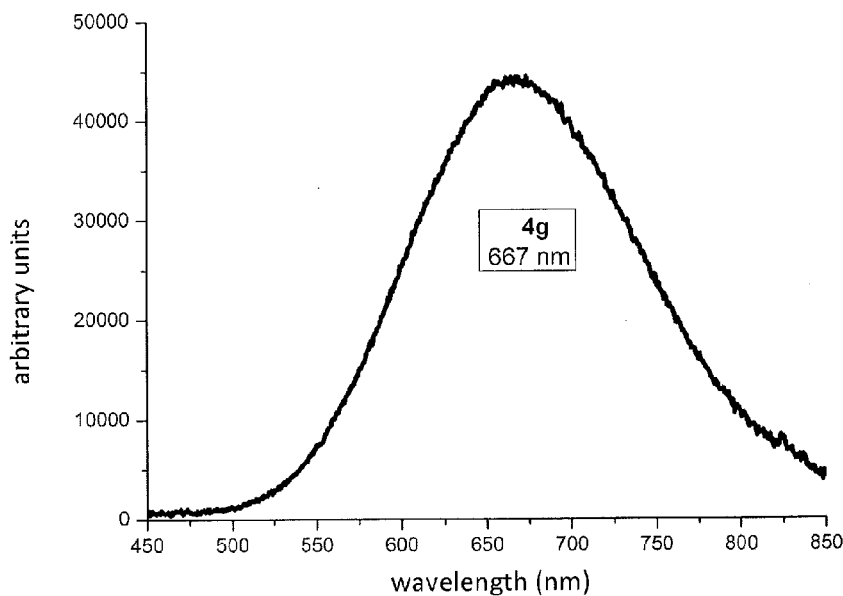
Figure 16: Crystal structure of 6a:
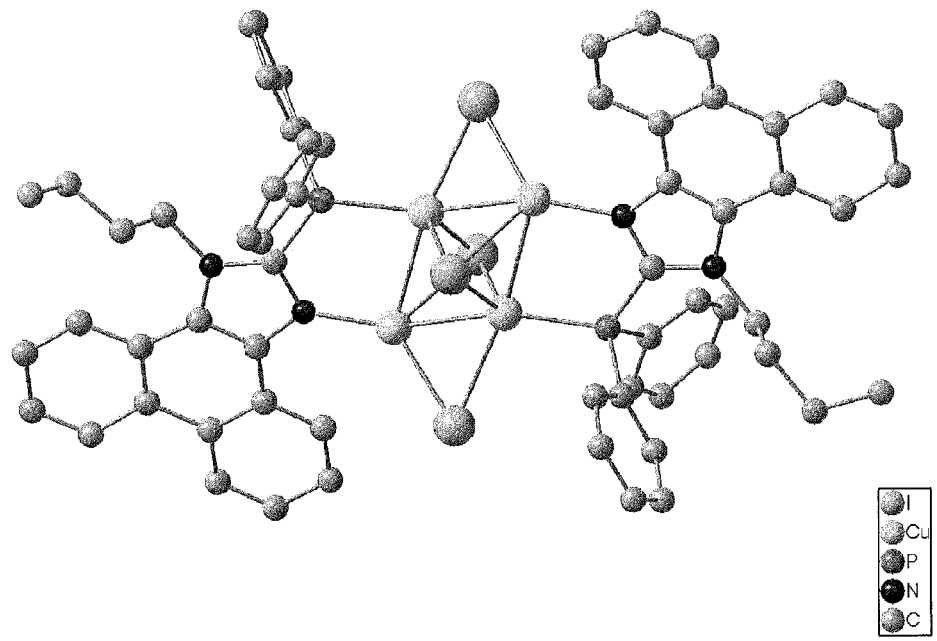

Figure 17: Emission spectrum of 6a:
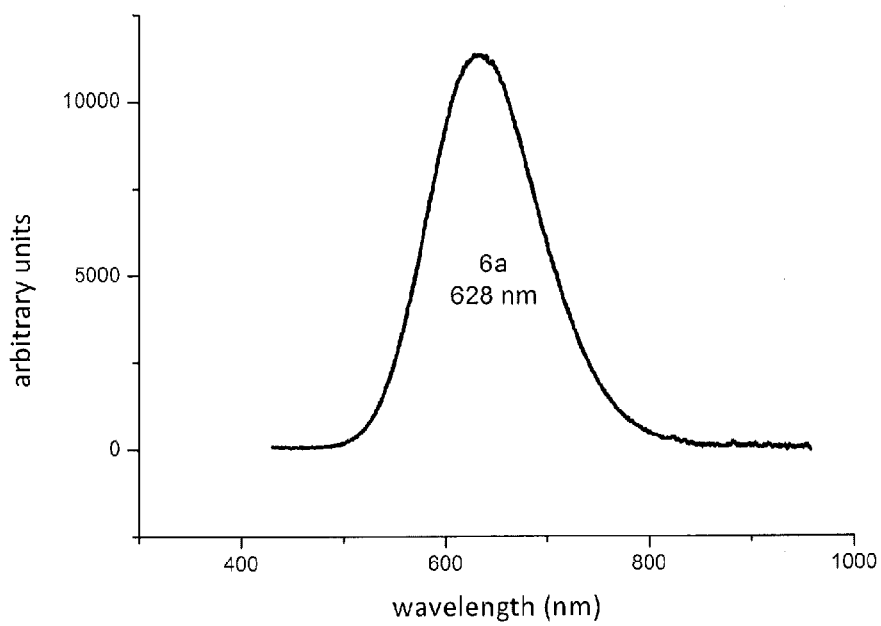
Figure 18: Emission spectrum of 6b:
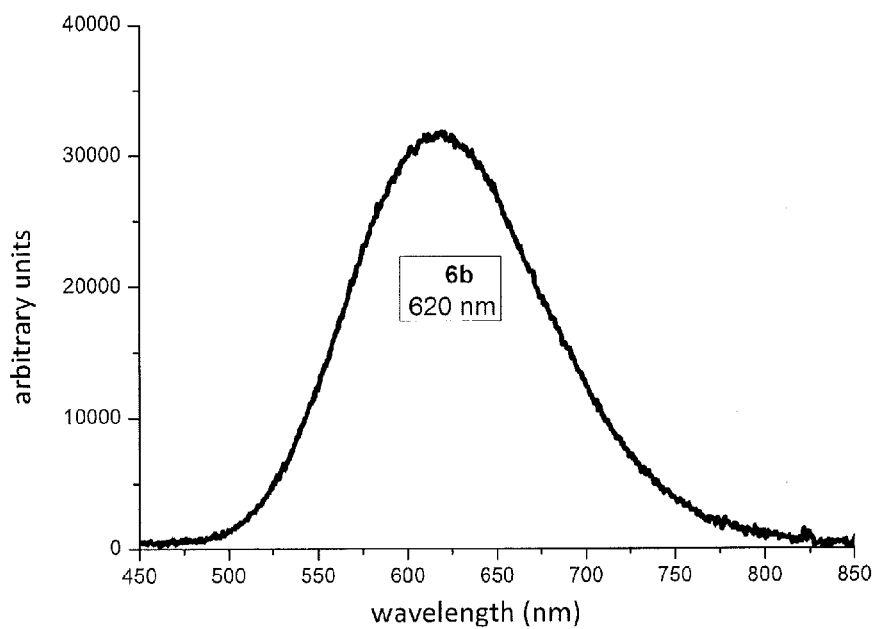

Figure 19: Emission spectrum of 6c:
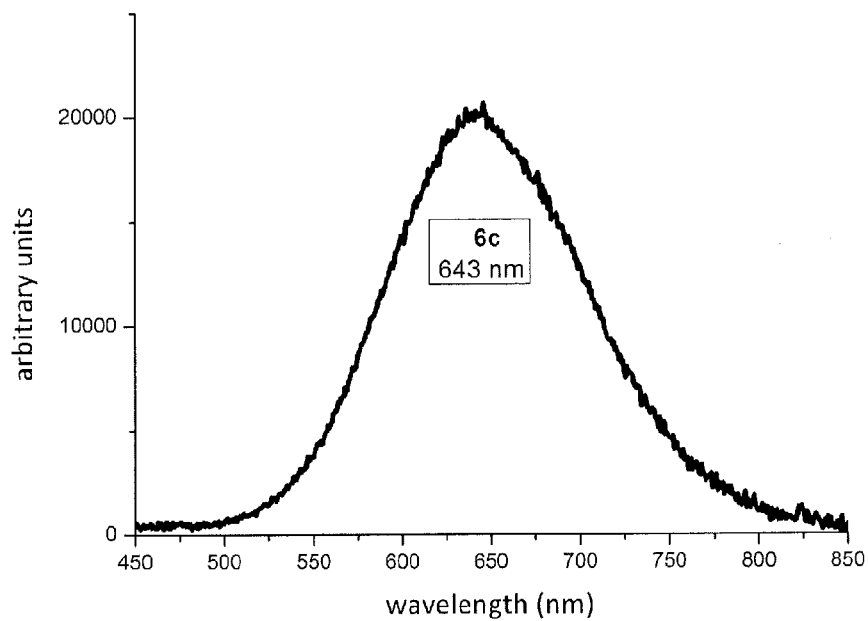
Figure 20: Emission spectrum of 6d:
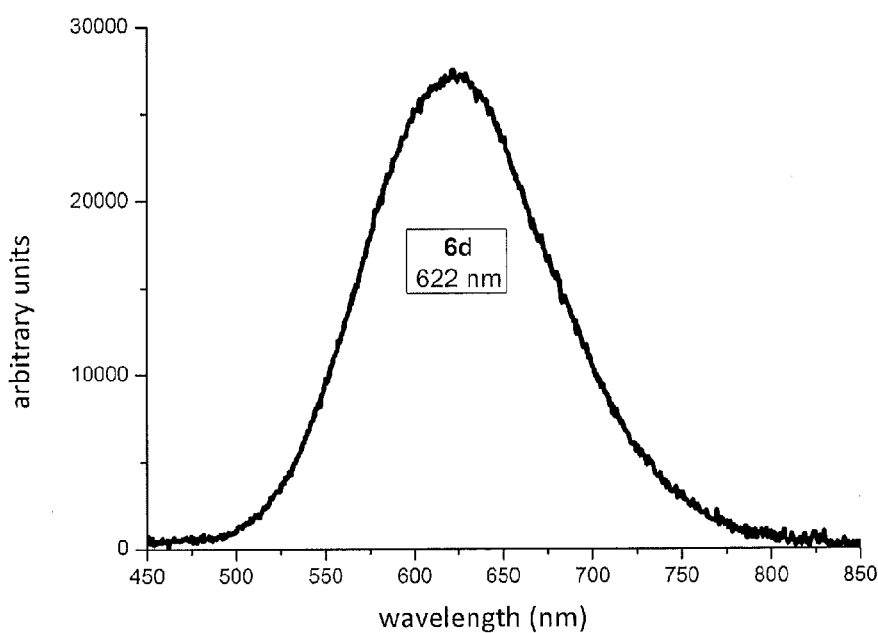

Figure 21: Emission spectrum of 8a:
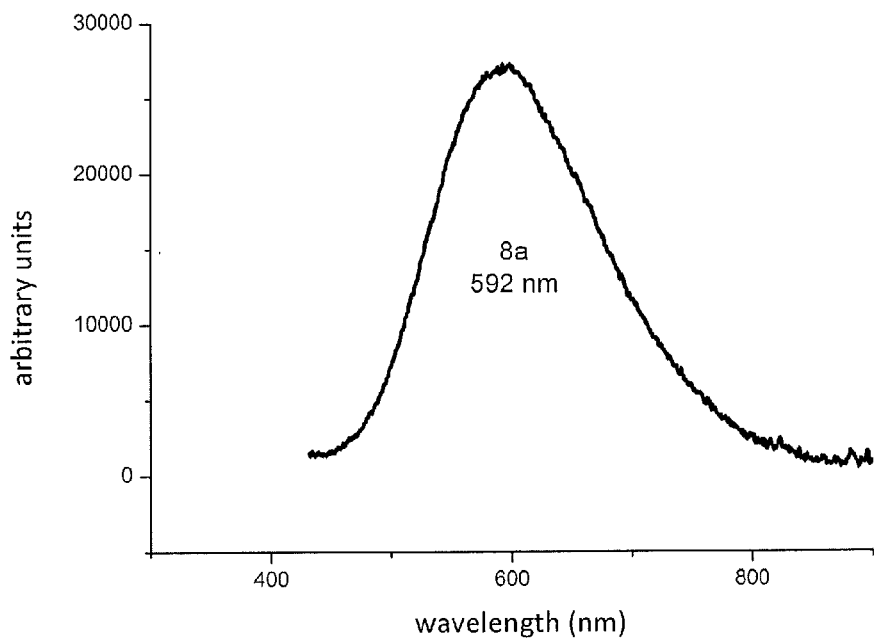
Figure 22: Emission spectrum of 8b:
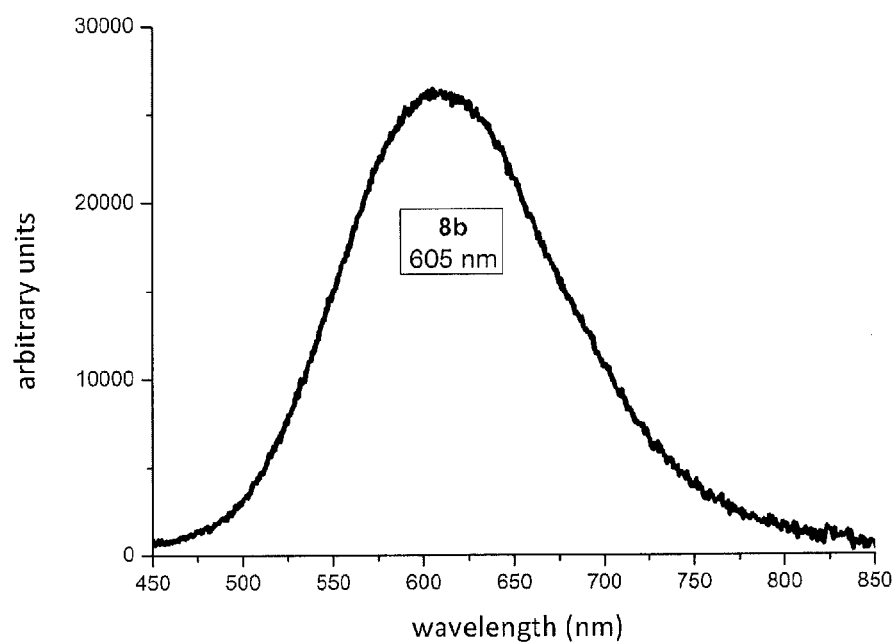

Figure 23: Emission spectrum of 8c:
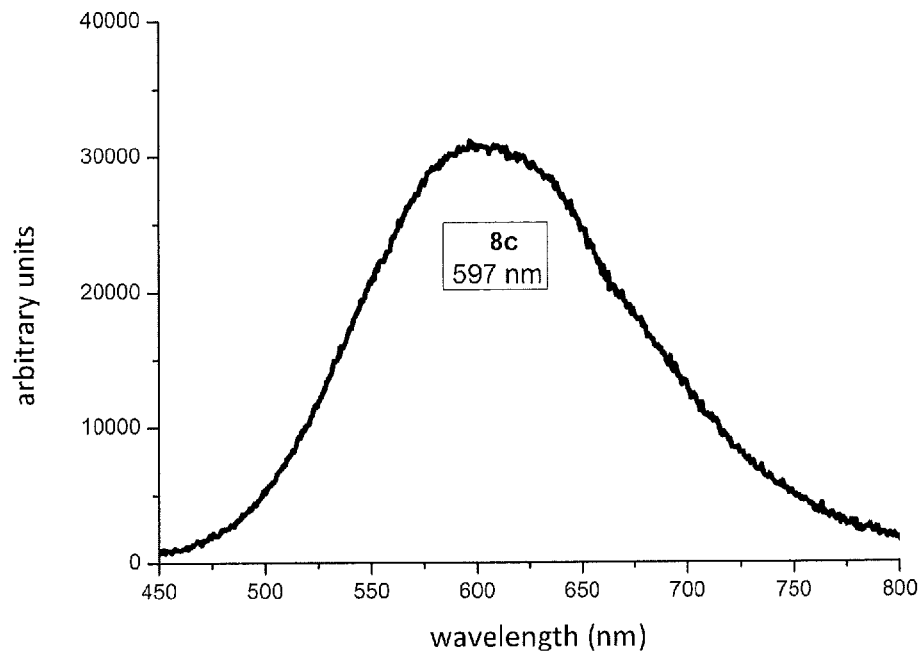
Figure 24: Emission spectrum of 10a:
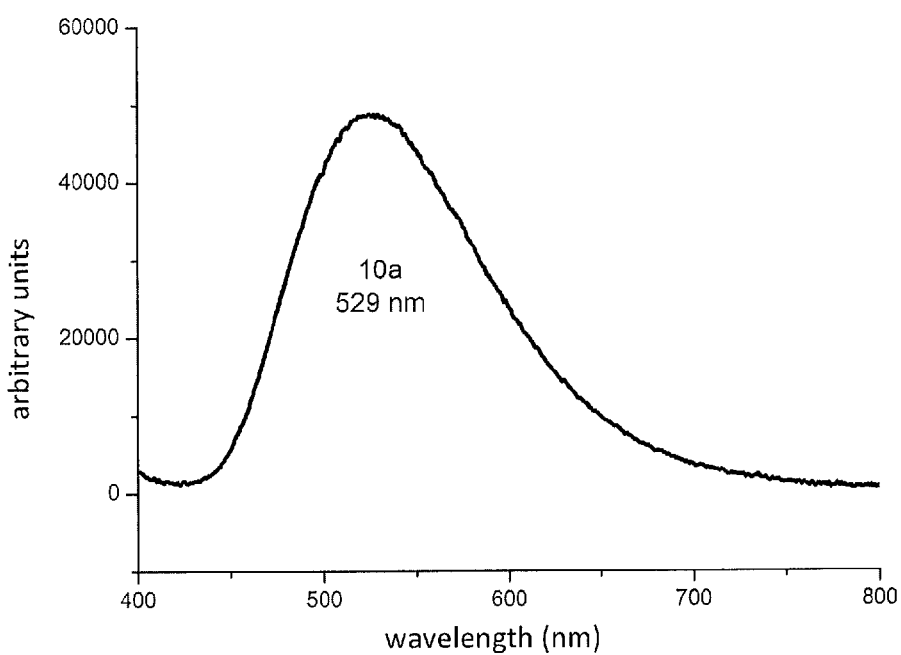

Figure 25: Crystal structure of 12a:
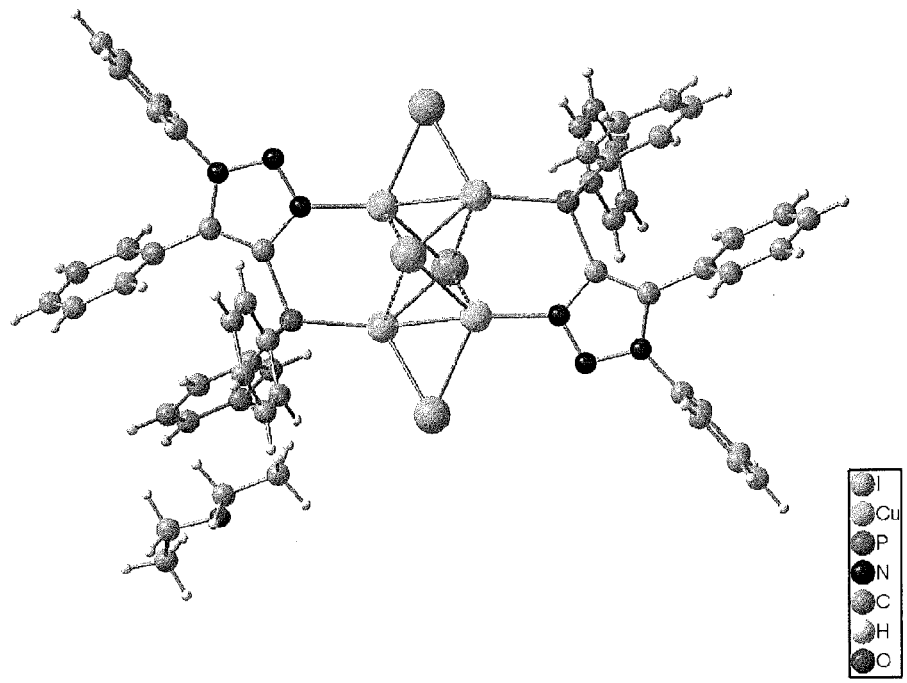
Figure 26: Emission spectrum of 14a:
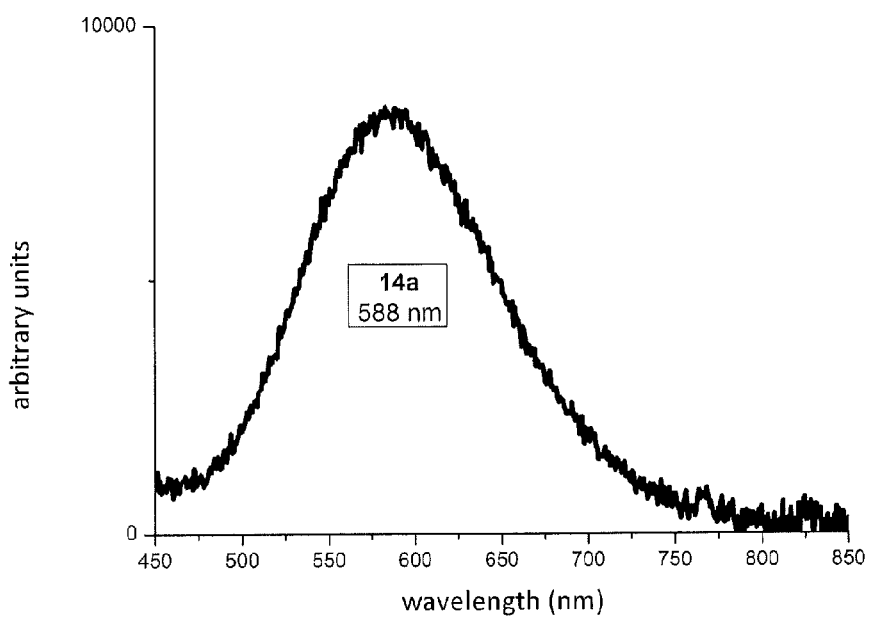

Figure 27: Emission spectrum of 14b:
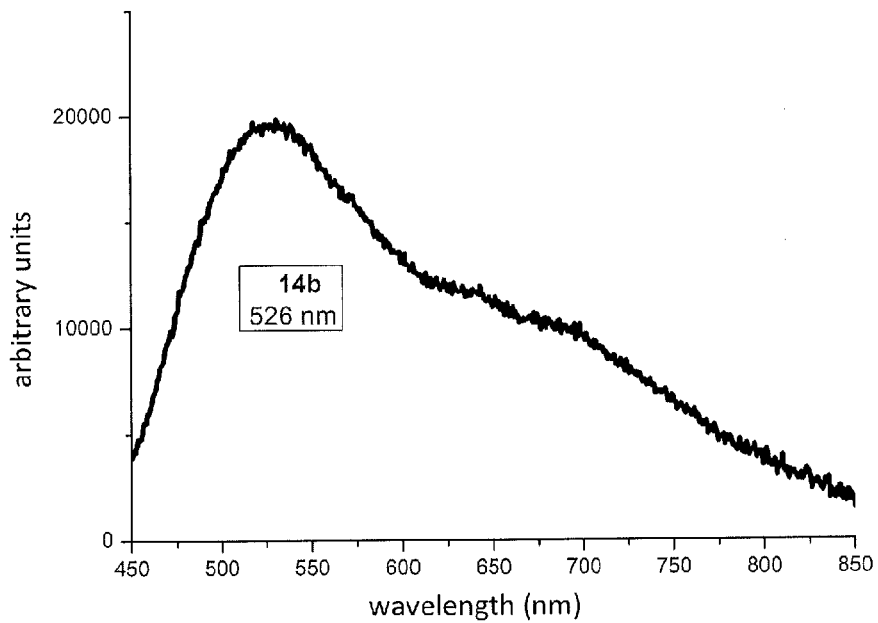
Figure 28: Emission spectrum of 14c:
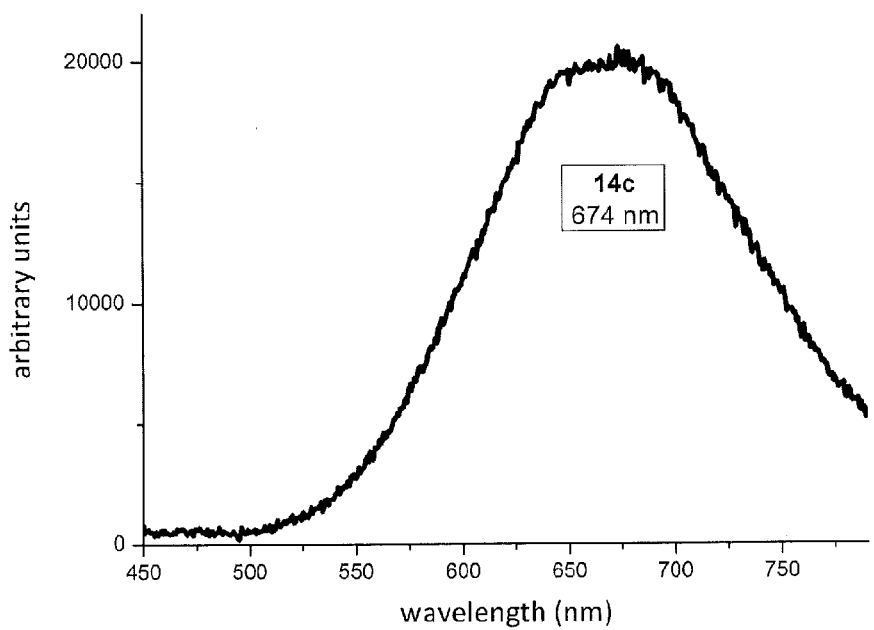

Figure 29: Emission spectrum of 14d:
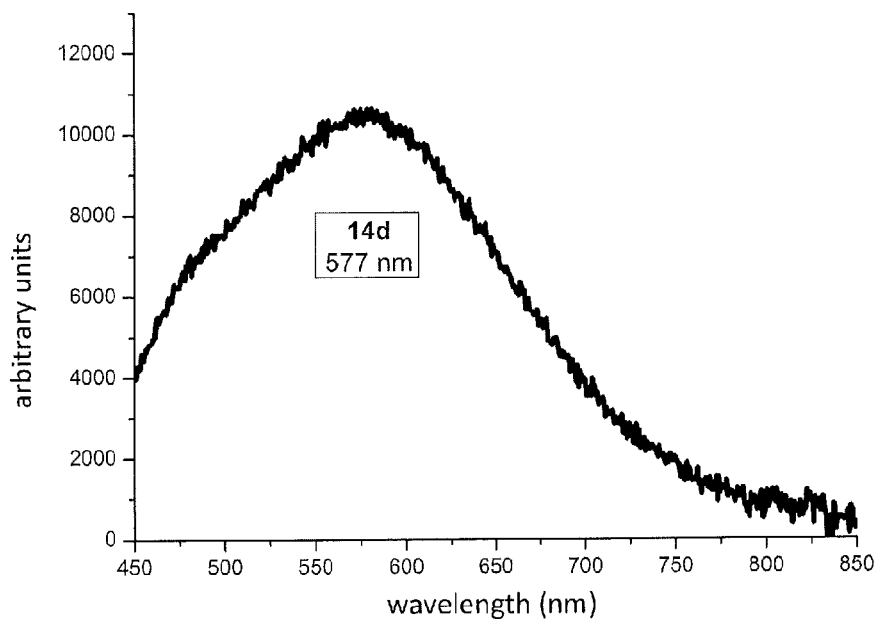
Figure 30: Emission spectrum of 14e:
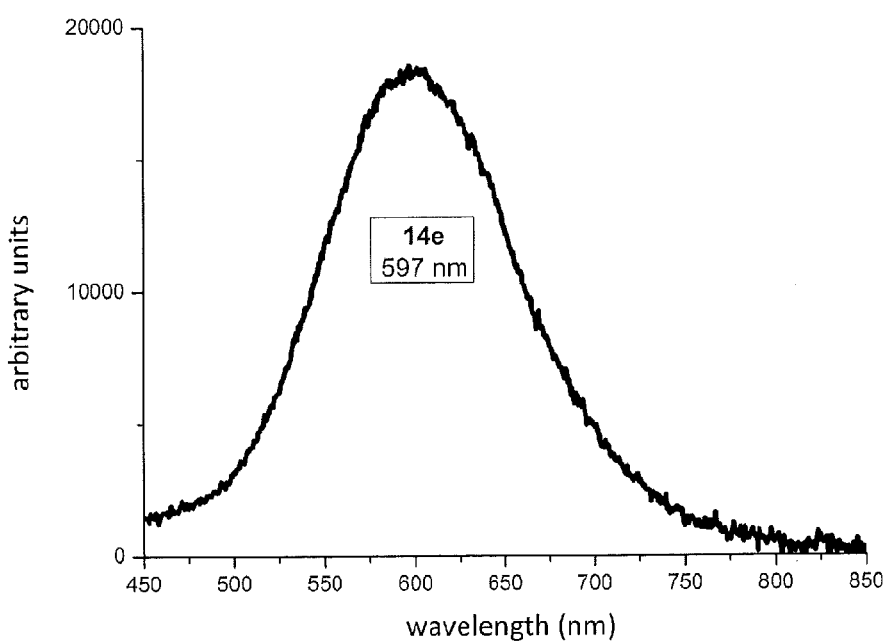

Figure 31: Emission spectrum of 18a:
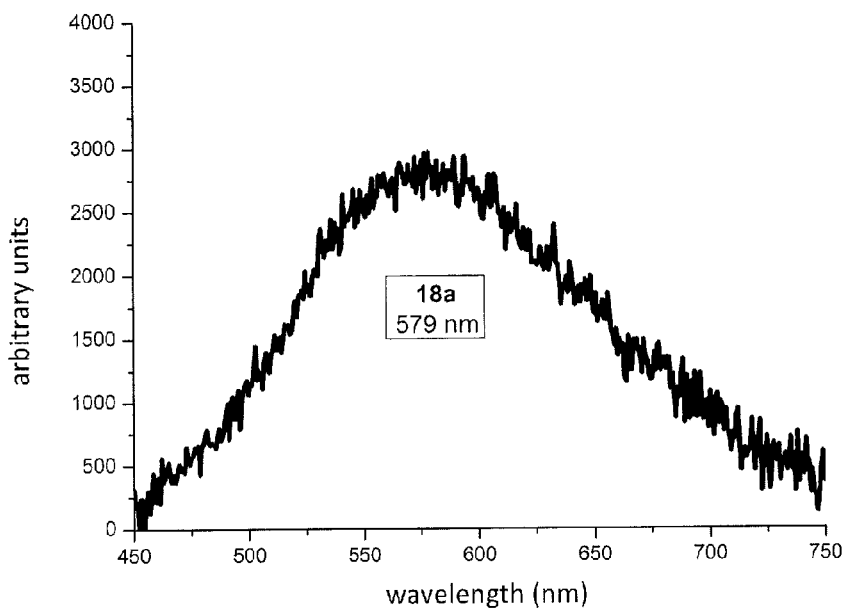
Figure 32: Crystal structure of 20e:
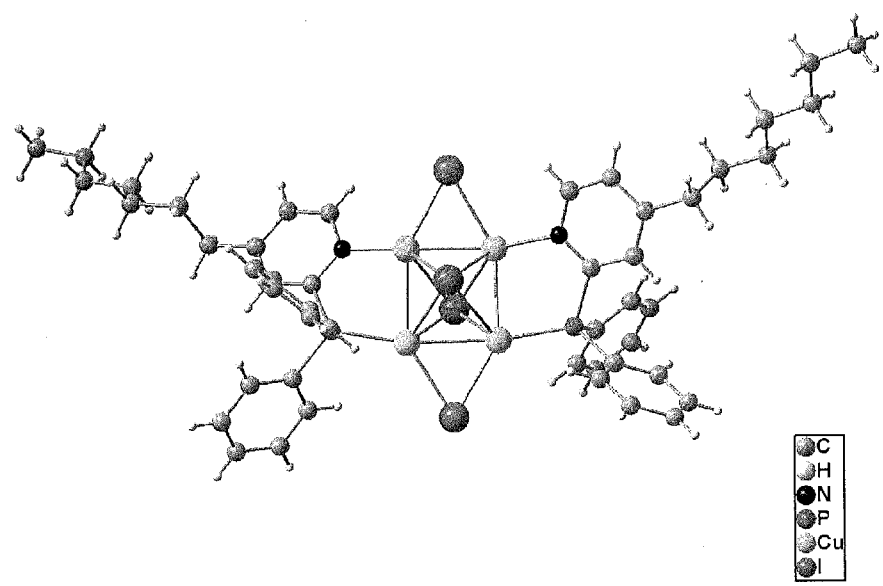

Figure 33: Emission spectrum of 20a:
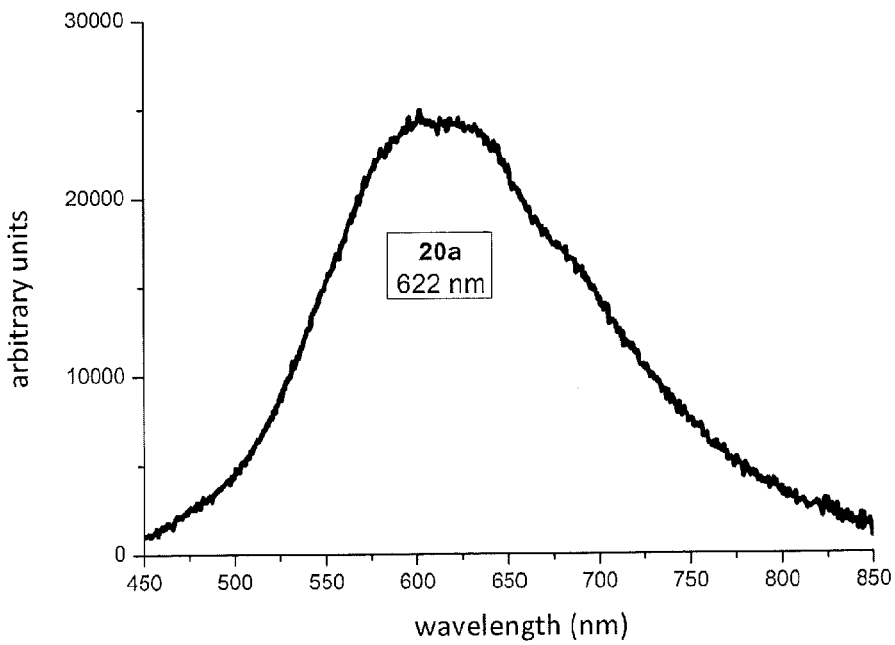
Figure 34: Emission spectrum of 20b:
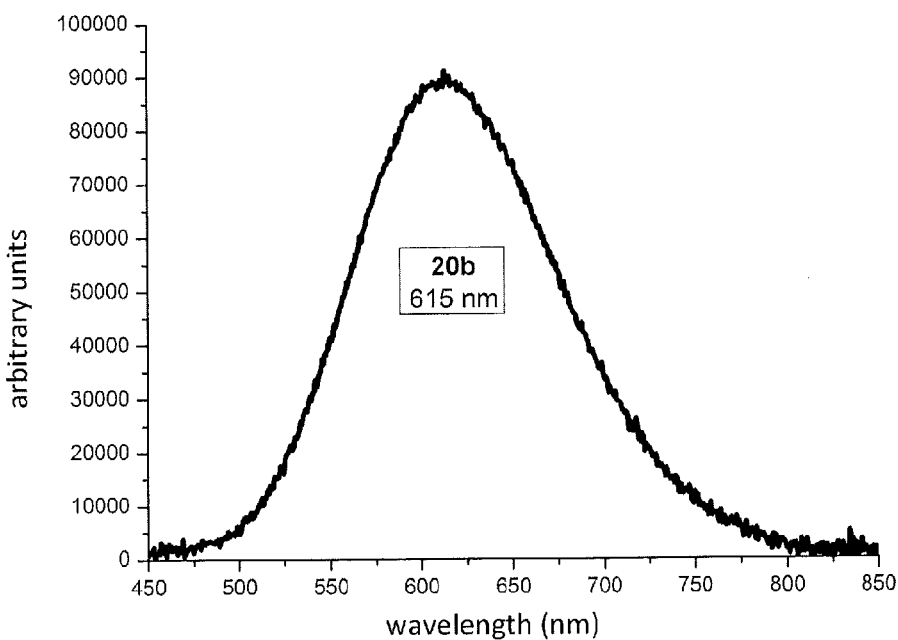

Figure 35: Emission spectrum of 20c:
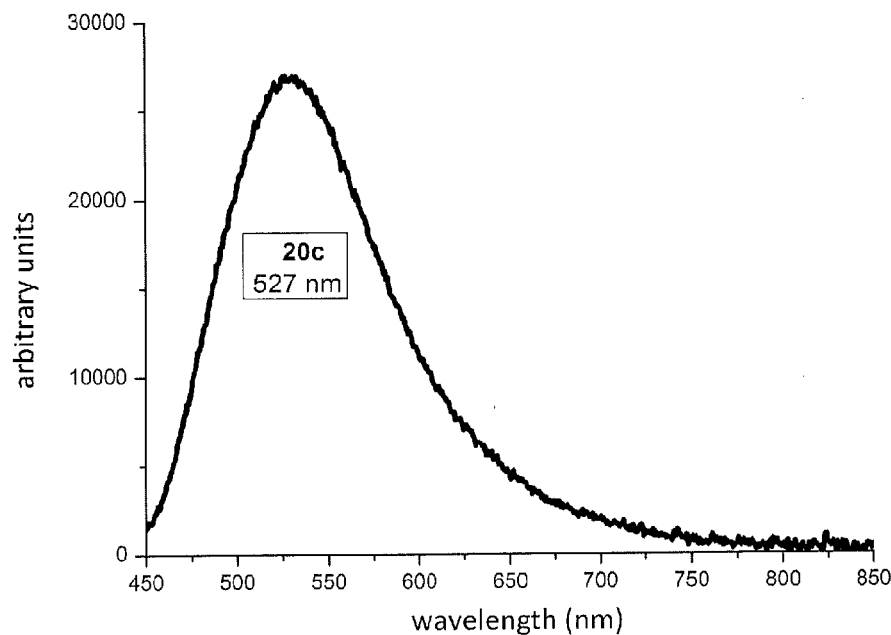
Figure 36: Emission spectrum of 20d:
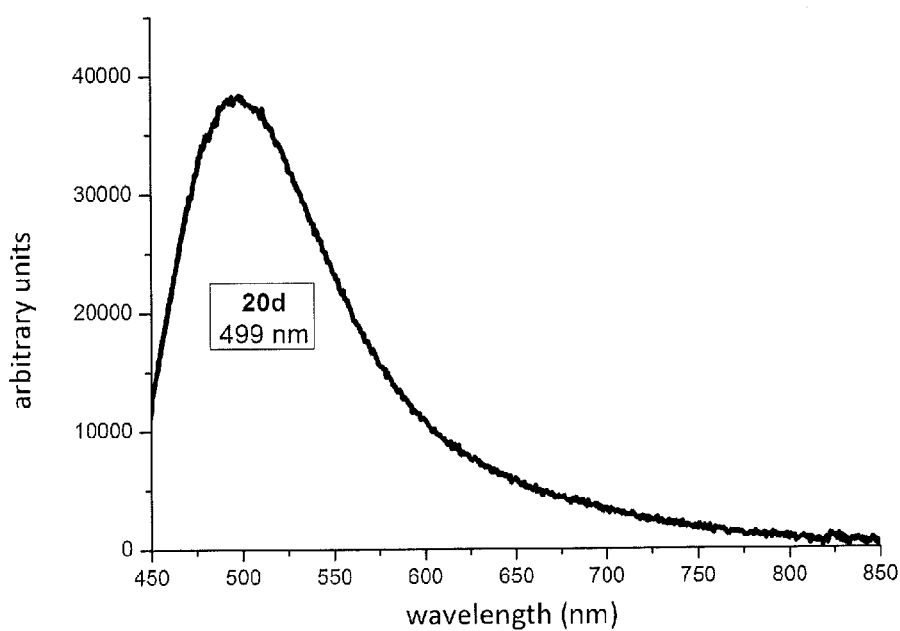

Figure 37: Emission spectrum of 20e:
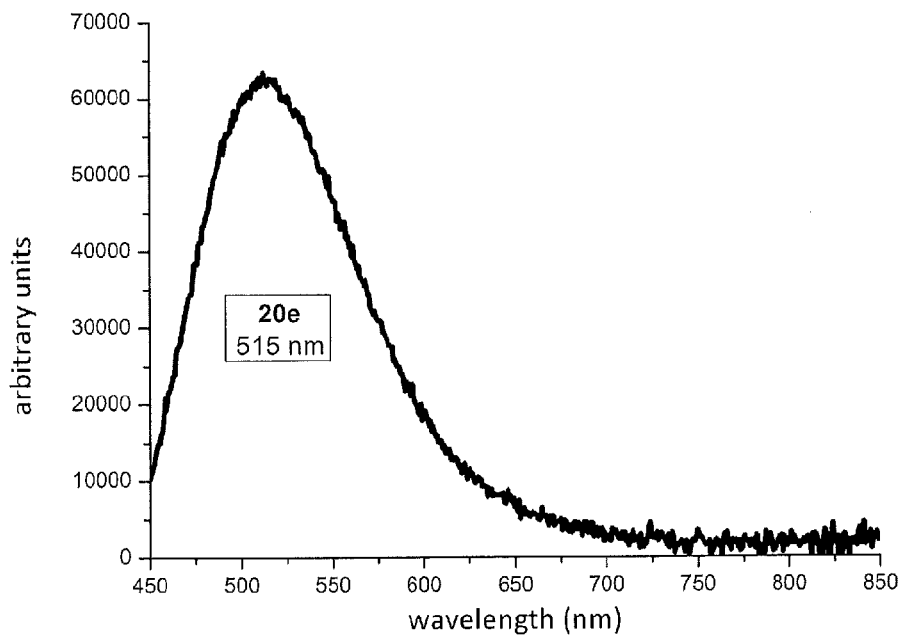
Figure 38: Emission spectrum of 20f:
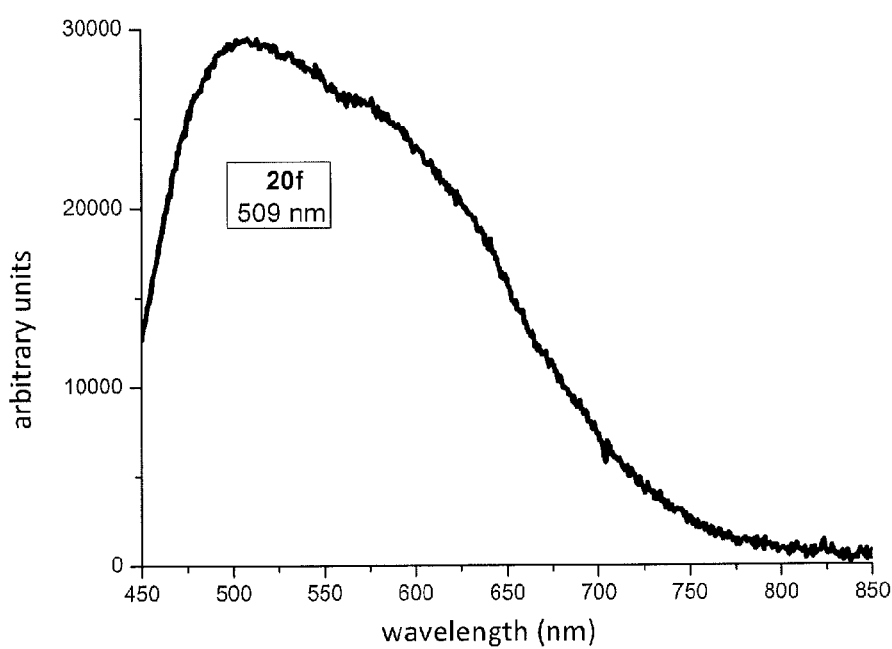

Figure 39: Emission spectrum of 20g:
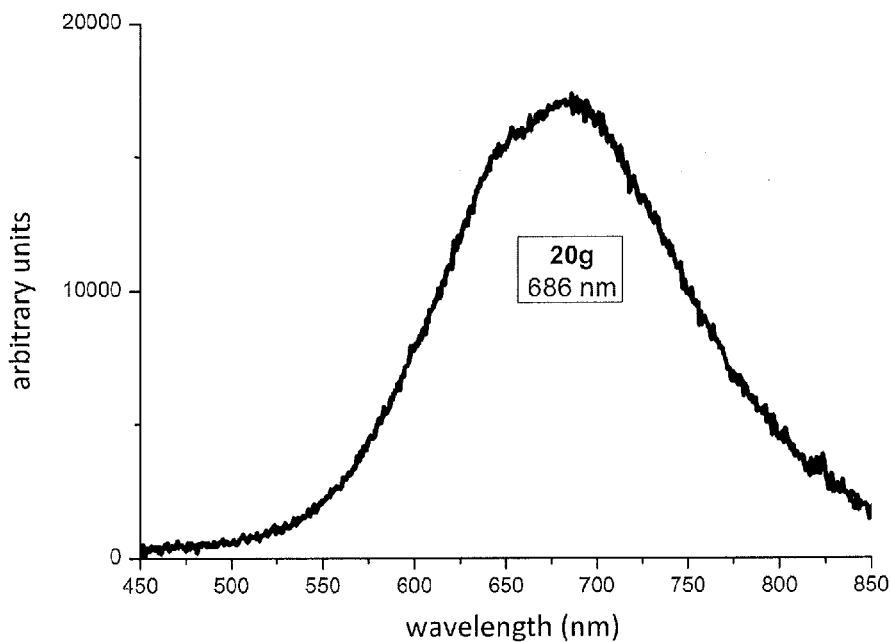
Figure 40: Emission spectrum of 22a:
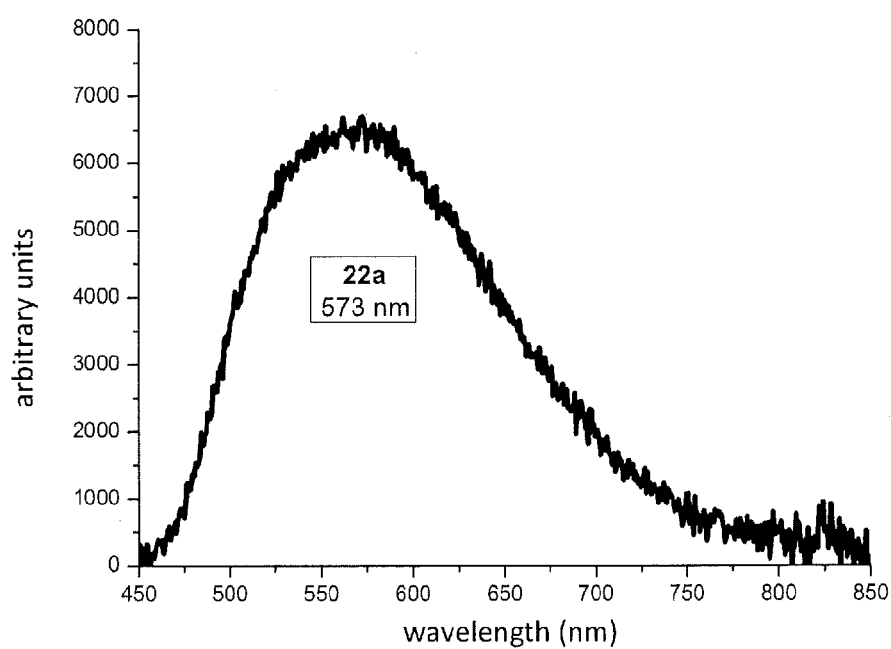

COPPER(I) COMPLEXES, IN PARTICULAR FOR OPTOELECTRONIC COMPONENTS

TECHNICAL FIELD

The invention relates to copper(I) complexes of the general formula A, in particular for use in optoelectronic components.

BACKGROUND

A dramatic change is currently on the horizon in the sector of visual display unit and illumination technology. It will be possible to manufacture flat displays or illuminated surfaces with a thickness of less than 0.5 mm. This new technology is based on the principle of OLEDs, Organic Light Emitting Diodes.

Such components consist predominantly of organic layers. At a voltage of, for example, 5 V to 10 V, electrons pass from a conductive metal layer, for example from an aluminum cathode, into a thin electron conduction layer and migrate in the direction of the anode. This consists, for example, of a transparent but electrically conductive thin indium tin oxide layer, from which positive charge carriers, so-called holes, migrate into an organic hole conduction layer. These holes move in the opposite direction compared to the electrons, namely towards the cathode. In a middle layer, the emitter layer, which likewise consists of an organic material, there are additionally special emitter molecules where, or close to which, the two charge carriers recombine and lead to uncharged but energetically excited states of the emitter molecules. The excited states then release their energy as bright emission of light, for example in a blue, green or red color. White light emission is also achievable. In some cases, it is also possible to dispense with the emitter layer when the emitter molecules are present in the hole or electron conduction layer.

Crucial for the construction of effective OLEDs are the light emitting materials (emitter molecules) used. These can be realized in different ways, namely by using purely organic or organometallic molecules as well as complex compounds. It can be shown that the light output of the OLEDs with organometallic substances, so-called triplet emitters, can be significantly greater than of purely organic materials. Due to this property, the further development of the organometallic materials is of high significance. Using organometallic complexes with high emission quantum yield (transitions including the lowermost triplet states to the singlet ground states), it is possible to achieve a particularly high efficiency of the device. These materials are often called triplet emitters or phosphorescent emitters.

Against this background, it was the object of the present invention to provide novel compounds, which are suitable for optoelectronic components.

BRIEF DESCRIPTION OF THE DRAWINGS

Exemplary embodiments of the present invention will be described below in more detail, with reference to the accompanying drawings, of which:

FIGS. 1-3 illustrate the crystal structures of compounds 2b, 2c and 2e, respectively.

FIGS. 4-7 illustrate the emission spectra of compounds 2a, 2b, 2c and 2e, respectively.

FIGS. 8-10 illustrate the crystal structures of compounds 4c, 4d and 4e, respectively.

FIGS. 11-15 illustrate the emission spectra of compounds 4a, 4c, 4d, 4f and 4g, respectively.

FIG. 16 illustrates the crystal structure of compound 6a.

FIGS. 17-20 illustrate the emission spectra of compounds 6a, 6b, 6c and 6d, respectively.

FIGS. 21-23 illustrate the emission spectra of compounds 8a, 8b and 8c, respectively.

FIG. 24 illustrates the emission spectrum of compound 10a.

FIG. 25 illustrates the crystal structure of compound 12a.

FIGS. 26-30 illustrate the emission spectra of compounds 14a, 14b, 14c, 14d and 14e, respectively.

FIG. 31 illustrates the emission spectrum of compound 18a.

FIG. 32 illustrates the crystal structure of compound 20e.

FIGS. 33-39 illustrate the emission spectra of compounds 20a, 20b, 20c, 20d, 20e, 20f and 20g, respectively.

FIG. 40 illustrates the emission spectrum of compound 22a.

DETAILED DESCRIPTION OF EXEMPLARY EMBODIMENTS OF THE INVENTION

Exemplary embodiments of the invention will now be discussed in further detail. This invention may, however, be embodied in many different forms and should not be construed as limited to the embodiments set forth herein.

The problem underlying the invention is solved by the provision of copper(I) complexes of the form $Cu_4X^*_4(E \cap N^*)_2$, which have a structure according to formula A:

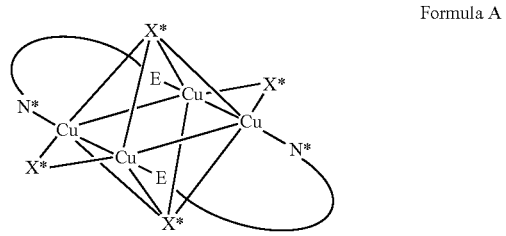

Formula A with:

$X^*$=Cl, Br, I, CN and/or SCN (i.e. independently of each other, so that the complex can have four identical or four different atoms $X^*$);

E=$R_2$As and/or $R_2$P, $N^* \cap E$=bidentate ligands with E=phosphanyl/arsenyl group of the $R_2$E form (with R=alkyl, aryl, alkoxyl, phenoxyl, amide); $N^*$=imine function. "⌒" is a carbon atom. E is in particular a $Ph_2$P-group (Ph=Phenyl), the imine function is part of a N-heteroaromatic 5- or 6-membered ring such as oxazole, imidazole, thiazole, isoxazole, isothiazole, pyrazole, 1,2,3-triazole, 1,2,3-oxadiazole, 1,2,5-oxadiazole, 1,2,3-thiadiazole, 1,2,5-thiadiazole, pyridine, pyrimidine, triazine, pyrazine or pyridazine. "⌒" is likewise part of this aromatic group. The carbon atom is directly adjacent to both the imine nitrogen atom and to the E atom. $N^* \cap E$ can optionally be substituted, in particular with groups which increase the solubility of the copper(I) complex in common organic solvents for the production of OLED components. Common organic solvents comprise, besides alcohols, ethers, alkanes as well as halogenated aliphatic and aromatic hydrocarbons and alkylated aromatic hydrocarbons in particular toluene, chlorobenzene, dichlorobenzene, mesitylene, xylene, tetrahydrofuran, phenetole, propiophenone.

A copper(I) complex according to the invention consists preferably of two identical ligands N*∩E, which reduces the synthetic effort and thus the production costs. The great advantage in the case of use of copper as the central metal is the low cost thereof, in particular compared to the metals such as Re, Os, Ir and Pt which are otherwise customary in OLED emitters. In addition, the low toxicity of copper also supports use thereof.

With regard to use thereof in optoelectronic components, the copper(I) complexes according to the invention are notable for a wide range of achievable emission colors. In addition, the emission quantum yield is high, especially greater than 50%. For emitter complexes with a Cu central ion, the emission decay times are astonishingly short.

In addition, the copper(I) complexes according to the invention are usable in relatively high emitter concentrations without considerable quenching effects. This means that emitter concentrations of 5% to 100% can be used in the emitter layer.

Preferably, the ligand N*∩E is oxazole, imidazole, thiazole, isoxazole, isothiazole, pyrazole, 1,2,3-triazole, 1,2,3-oxadiazole, 1,2,5-oxadiazole, 1,2,3-thiadiazole, 1,2,5-thiadiazole, pyridine, pyrimidine, triazine, pyrazine and/or pyridazine, which each can be substituted, as described herein.

Preferably the ligand N*∩E is the following ligands:

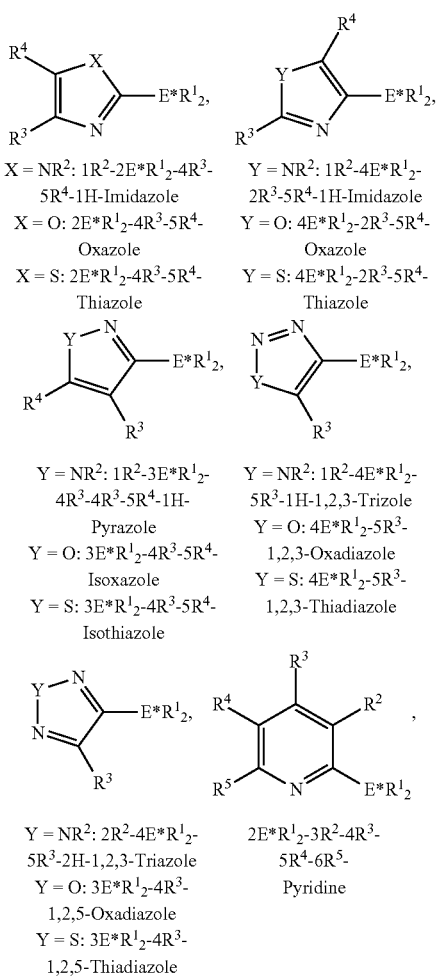

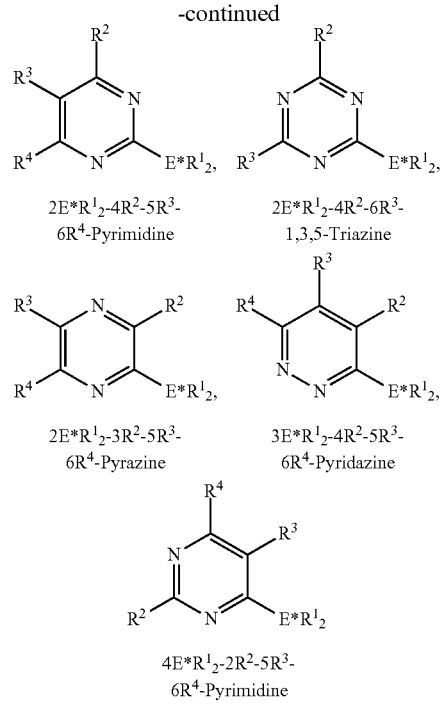

with
X=O or $NR^2$
Y=O or $NR^2$ or S
E*=As or P

R1-R5 can be, each independently from each other, hydrogen, halogen or substituents which are bound via oxygen (—OR), nitrogen (—$NR_2$) or silicon atoms (—$SiR_3$) as well as alkyl- (also branched or cyclic), aryl-, heteroaryl-, alkenyl-, alkinyl-groups and respectively substituted alkyl- (also branched or cyclic), aryl-, heteroaryl- and alkenyl-groups with substituents such as halogens or deuterium, alkyl groups (also branched or cyclic), and further generally known donor and acceptor groups such as for example amines, carboxylates and their esters, and $CF_3$-groups. R2-R5 can optionally also lead to annulated ring systems.

Particularly preferably the ligand N*∩E is the following ligands:

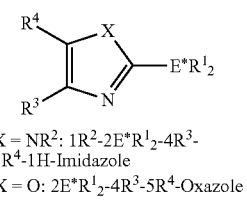

X = $NR^2$: $1R^2$-$2E^*R^1_2$-$4R^3$-
    $5R^4$-1H-Imidazole
X = O: $2E^*R^1_2$-$4R^3$-$5R^4$-Oxazole wherein the symbols used are described above.

The invention also relates to a method for producing a copper(I) complex according to the invention. This method according to the invention comprises the step of performing a reaction of N*∩E with Cu(I)X*,
wherein
X*=Cl, Br, I, CN, and/or SCN (independently from each other)
N*∩E=a bidentate ligand with
E=phosphanyl/arsenyl group of the $R_2E$ form (with R=alkyl, aryl, alkoxyl, phenoxyl, or amide);

N*=imine function, which is part of a N-hereroaromatic 5- or 6-membered ring such as oxazole, imidazole, thiazole, isoxazole, isothiazole, pyrazole, 1,2,3-triazole, 1,2,3-oxadiazole, 1,2,5-oxadiazole, 1,2,3-thiadiazole, 1,2,5-thiadiazole, pyridine, pyrimidine, triazine, pyrazine and/or pyridazine.

"∩"=at least one carbon atom which is likewise part of the aromatic group, wherein the carbon atom is directly adjacent both to the imine nitrogen atom and to the phosphorus or arsenic atom.

The at least one substituent for increasing the solubility of the complex in organic solvents, optionally present at the ligand N*∩E, is described further below.

The reaction is performed preferably in dichloromethane (DCM). A solid can be obtained by addition of diethyl ether to the dissolved product. The latter can be conducted by precipitation or inward diffusion or in an ultrasound bath.

In the reaction of 2 units of bidentate P∩N*-ligands (P∩N*=phosphine ligand, definition see below) with 4 units Cu(I)X* (X*=Cl, Br, I, CN, SCN), preferably in dichloromethane (DCM), preferably at room temperature, the tetranuclear 4:2-complex $Cu_4X^*_4(P∩N^*)_2$ is formed, in which the four Cu atoms form the base area of an octahedron and two halogen ions form its top (eq. 1). The other two halogen ions bridge two opposing sides of the base area of the octahedron, whereas the two P∩N*-ligands bridge the two other opposite sides of the base area of the octahedron in a chelating way with the N atom as well as the P atom and thereby coordinatively saturate the Cu atoms.

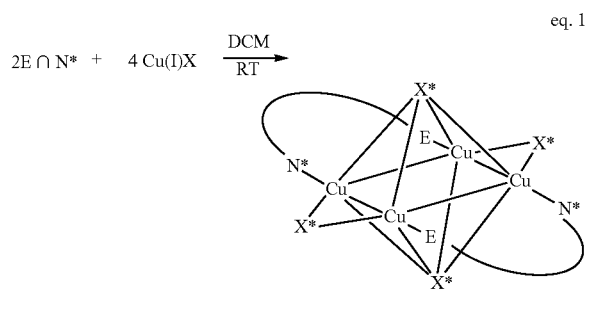

eq. 1

$2 E∩N^* + 4 Cu(I)X \xrightarrow[RT]{DCM}$

Thus, the complex is obtainable in only one step by reaction of Cu(I)X* with the bidentate P∩N* ligand. The complex can be isolated by precipitation with $Et_2O$ as white microcrystalline powder. Single crystals can be obtained by slow diffusion of $Et_2O$ into the reaction solution. The identities of the complexes were clearly determined by elementary analyses and X-ray structure analyses.

This is the general formula A shown above. The bidentate E∩N* ligands can comprise each independently at least one substituent: The substituents can be, each independently from each other, hydrogen, halogen or substituents which are bound via oxygen (—OR), nitrogen (—$NR_2$) or silicon atoms (—$SiR_3$) as well as alkyl- (also branched or cyclic), aryl, heteroaryl, alkenyl, akinyl groups or respectively substituted alkyl (also branched or cyclic), aryl, heteroaryl and alkenyl groups with substituents such as halogens or deuterium, alkyl groups (also branched or cyclic), and further generally known donor and acceptor groups such as for example amines, carboxylates and their esters, and $CF_3$- groups. The substituents can optionally also lead to annulated ring systems.

Solubility

When manufacturing optoelectronic components using wet-chemical processes, it is advantageous to specifically regulate the solubility. Thereby, the complete or partial dissolving of a layer already deposited can be avoided. By introducing special substituents, the solubility characteristics can be strongly influenced. Thereby, it is possible to use orthogonal solvents that dissolve only the substances of the instant manufacturing step, but not the substances of the layer(s) below. For this purpose the substituents R2-R5 can be selected such that they allow tuning of the solubilities. The following possibilities for the selection of corresponding substituents are given:

Solubility in Nonpolar Media

Nonpolar substituents R2-R5 increase the solubility in nonpolar solvents and decrease the solubility in polar solvents. Nonpolar groups are for example alkyl groups [$CH_3$—($CH_2$)$_n$—] (n=1-30), also branched or cyclic, substituted alkyl groups, e.g. with halogens. Hereby particularly highlighted are: partly or perfluorinated alkyl groups as well as perfluorinated oligo- and polyether, e.g. [—($CF_2$)$_2$—O]$_n$— and (—$CF_2$—O)$_n$— (n=2-500). Further nonpolar groups are: ethers —OR*, thioethers —SR*, differently substituted silanes $R^*_3Si$— (R*=alkyl or aryl), siloxanes $R^*_3Si$—O—, oligosiloxanes $R^{}$(—$R_2Si$—O)$_n$— ($R^{}$=R*, n=2-20), polysiloxanes $R^{**}$(—$R^*_2Si$—O)$_n$— (n>20); oligo/polyphosphazenes $R^{**}$(—$R^*_2P$=N—)$_n$— (n=1-200).

Solubility in Polar Media

Polar substituents R2-R5 increase the solubility in polar solvents. These can be:
alcohol-groups: —OH
carboxylic acid, phosphonic acid, sulfonic acid groups as well as their salts and esters (R*=H, alkyl, aryl, halogen; cations: alkali metals, ammonium salts):
—COOH, —P(O)(OH)$_2$, —P(S)(OH)$_2$, —S(O)(OH)$_2$, —COOR*, —P(O)(OR*)$_2$, —P(S)(OR*)$_2$, —S(O)(OR*)$_2$, —CONHR*, —P(O)(NR*$_2$)$_2$, —P(S)(NR*$_2$)$_2$, —S(O)(NR*$_2$)$_2$
sulfoxides: —S(O)R*, —S(O)$_2$R*
carbonyl groups: —C(O)R*
amines: —$NH_2$, —NR*$_2$, —N($CH_2CH_2OH$)$_2$,
hydroxylamines =NOR*
oligoesters, —O($CH_2O$—)$_n$, —O($CH_2CH_2O$—)$_n$ (n=2-200)
positively charged substituents: e.g. ammonium salts —N$^+$R*$_3$X$^-$, phosphonium salts —P$^+$R*3X$^-$
negatively charged substituents, e.g. borates —(BR*$_3$)$^-$, aluminates —(AlR*$_3$)$^-$ (an alkali metal or ammonium ion can act as anion).

In order to increase the solubility of the copper(I) complexes according to the invention in organic solvents, optionally at least one of the structures N*∩E is substituted preferably with at least one substituent. The substituent can be chosen from the group consisting of:
long-chained, branched or unbranched or cyclic alkyl chains with a length of C1 to C30, preferably with a length of C3 to C20, particularly preferably with a length of C5 to C15,
long-chained, branched or unbranched or cyclic alkoxy chains with a length of C1 to C30, preferably with a length of C3 to C20, particularly preferably with a length of C5 to C15,
branched or unbranched or cyclic perfluoro alkyl chains with a length of C1 to C30, preferably with a length of C3 to C20, particularly preferably with a length of C5 to C15 and short-chained polyethers, such as for example polymers in the form of $(-OCH_2CH_2O-)_n$, with n<500. Examples are polyethylene glycols (PEG), which can be applied as chemical inert, watersoluble and non-toxic polymers with a chain length of 3-50 repeating units.

In one preferred embodiment of the invention, the alkyl chains or alkoxy chains or perfluoro alkyl chains are modified by polar groups, e.g. by alcohols, aldehydes, acetals, amines, amidines, carboxylic acids, carboxylic acid esters, carboxylic acid amides, imides, carboxylic acid halides, carboxylic acid anhydrides, ethers, halogens, hydroxamic acids, hydrazines, hydrazones, hydroxyl amines, lactones, lactams, nitriles, isocyanides, isocyanates, isothiocyanates, oximes, nitrosoaryls, nitroalkyls, nitroaryls, phenols, phosphoric acid esters and/or phosphonic acid, thiols, thioethers, thioaldehydes, thioketones, thioacetals, thiocarboxylic acids, thioester, dithio acid, dithio acid ester, sulfoxides, sulfones, sulfonic acid, sulfonic acid esters, sulfinic acid, sulfinic acid ester, sulfenic acid, sulfenic acid ester, thiosulfinic acid, thiosulfinic acid ester, thiosulfonic acid, thiosulfonic acid ester, sulfonamides, thiosulfonamides, sulfinamides, sulfenamides, sulfates, thiosulfates, sultones, sultames, trialkylsilyl and triarylsilyl groups as well as trialkoxysilyl groups, which lead to an additional increase in solubility.

A very distinct increase in solubility is achieved from at least one C6 unit, branched or unbranched or cyclic. Substitution e.g. with a linear C6 chain (see below) leads to a very good solubility in e.g. dichloromethane and to a good solubility in dichlorobenzene or chlorobenzene.

Optionally, the method of preparation can comprise the step that at least one ligand N*∩E is substituted with at least one substituent for increasing the solubility in the desired organic solvent, whereat in one embodiment of the invention the substituent can be chosen from the groups described above.

In accordance with the invention are also copper(I) complexes which can be prepared by such a synthesis method.

The copper(I) complexes of formula A can be applied according to the invention as emitter materials in an emitter layer of a light emitting optoelectronic component. The optoelectronic components are preferably the following: organic light emitting components (OLEDs), light emitting electrochemical cells, OLED-sensors (in particular in gas and vapor sensors which are not hermetically screened from the outside), organic solar cells, organic field-effect transistors, organic lasers and down-conversion elements.

In one embodiment of the invention the ratio of the copper(I) complex in the emitter layer or absorber layer in such an optoelectronic component is 100%. In an alternative embodiment the ratio of the copper(I) complex in the emitter layer or absorber layer is 1% to 99%.

In one method for the manufacture of an optoelectronic component, in which a copper(I) complex according to the invention is used, the application of such a copper(I) complex on a carrier material can be carried out. This application can be carried out by wet-chemical means, by means of colloidal suspension or by means of sublimation.

Another aspect of the invention relates to a method for altering the emission and/or absorption properties of an electronic component. Thereby, a copper(I) complex according to the invention is introduced into a matrix material for conduction of electrons or holes into an optoelectronic component.

Another aspect of the invention relates to the use of a copper(I) complex according to the invention, particularly in an optoelectronic component, for conversion of UV radiation or of blue light to visible light, especially to green, yellow or red light (down-conversion).

In another aspect the invention relates to a bidentate ligand of formula B, in particular for the production of a copper complex of formula A, as well as the method for the preparation of such a ligand.

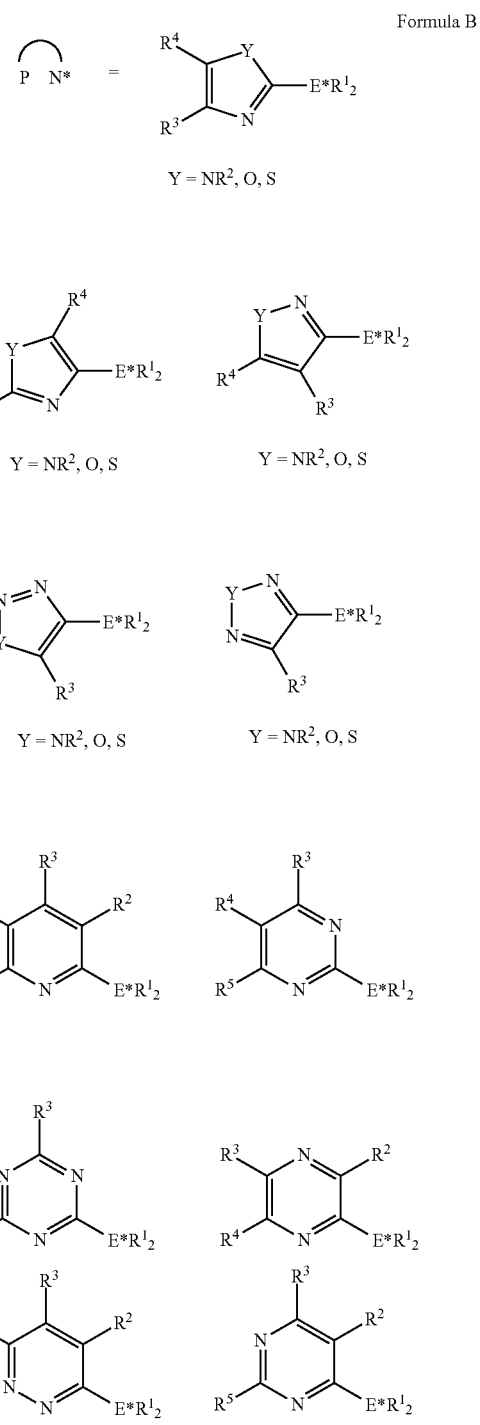

Formula B

The symbols used in formula B correspond to the symbols used in formula A, which are described herein.

The method for preparing a bidentate ligand of formula B is performed according to the scheme shown below:
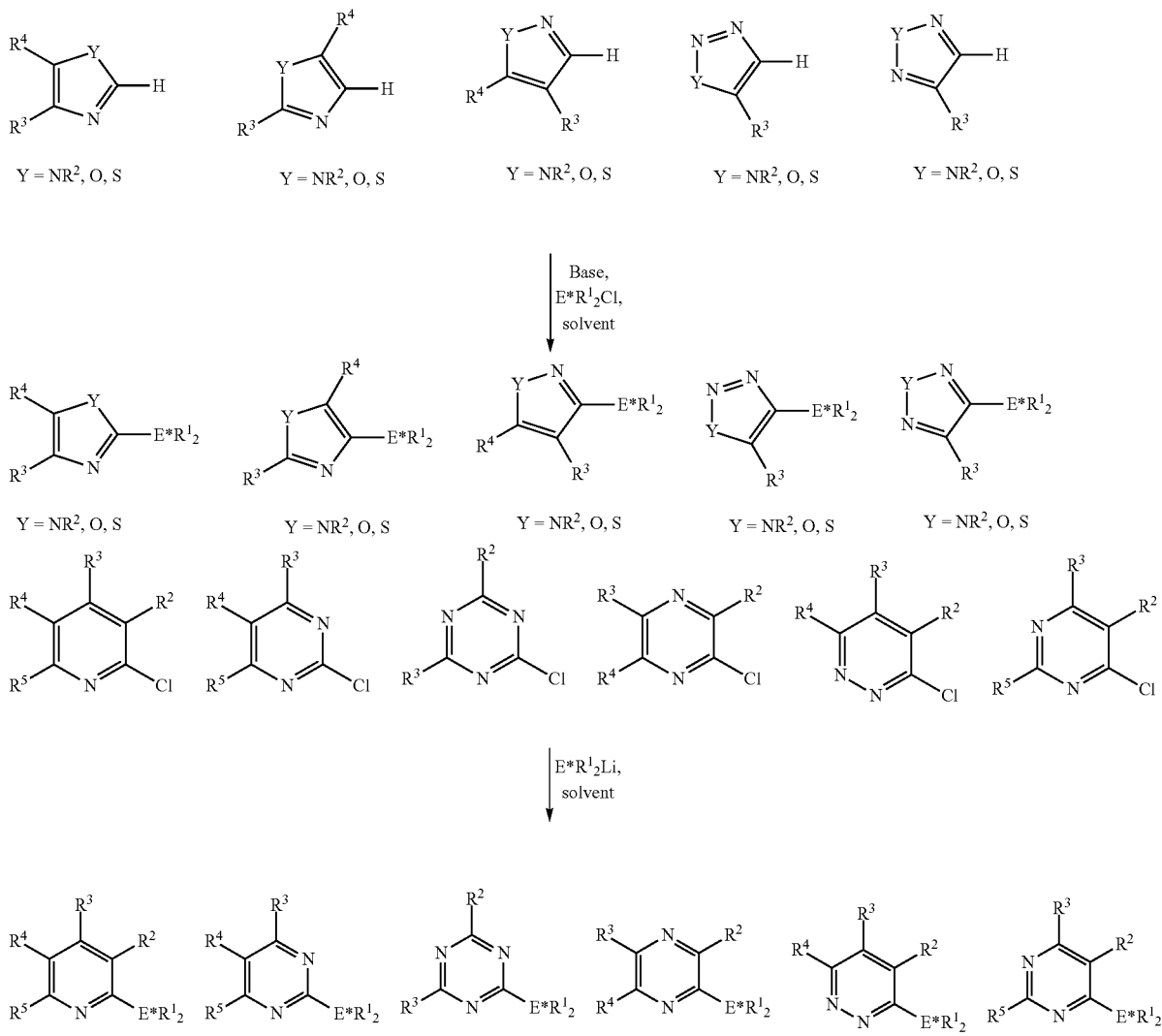
Preferably, the method for preparing a bidentate ligand of formula B is performed according to one of the schemes shown below:
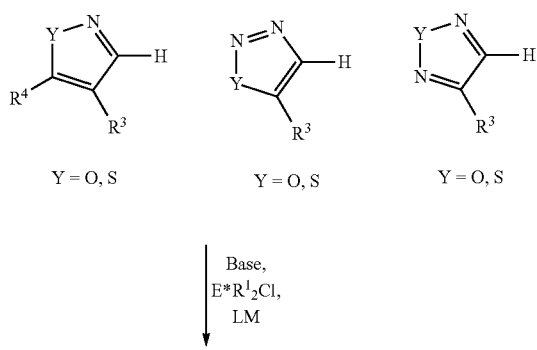

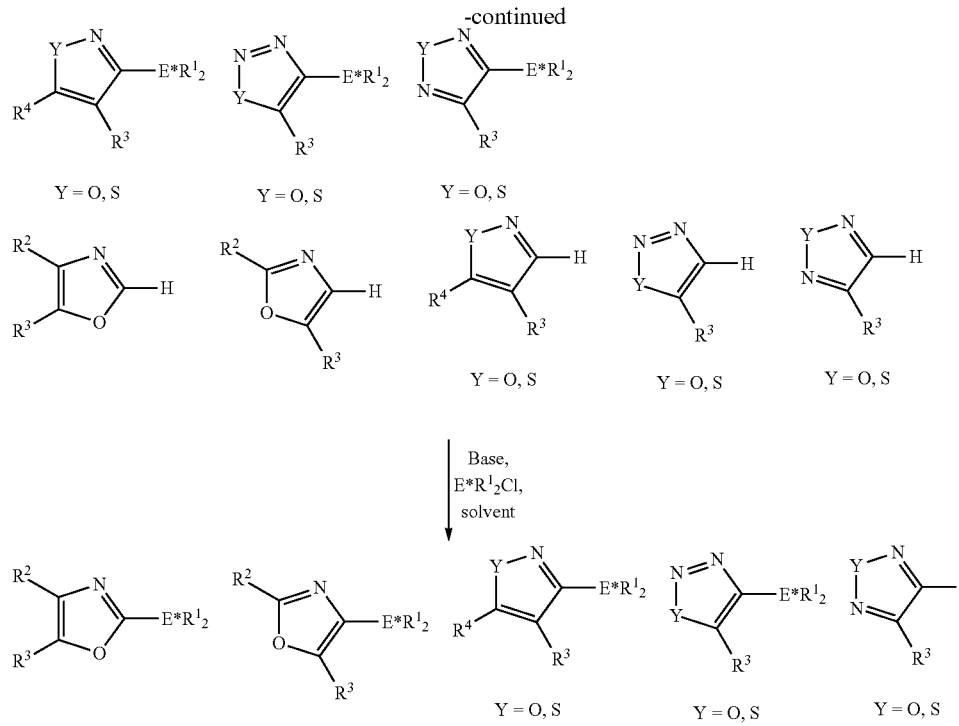

Y = O, S

The symbols used above correspond to the symbols used in formula A, which are described herein.

EXAMPLES

In the examples shown here the ligand E∩N* of the general formula A is a ligand P∩N* (with E=Ph$_2$P).

The bidentate phosphine ligands oxazole, imidazole, thiazole, isoxazole, isothiazole, pyrazole, 1,2,3-triazole, 1,2,3-oxadiazole, 1,2,5-oxadiazole, 1,2,3-thiadiazole, 1,2,5-thiadiazole, pyridine, pyrimidine, triazine, pyrazine, pyridazine were used for the preparation of the copper complexes according to the description above:

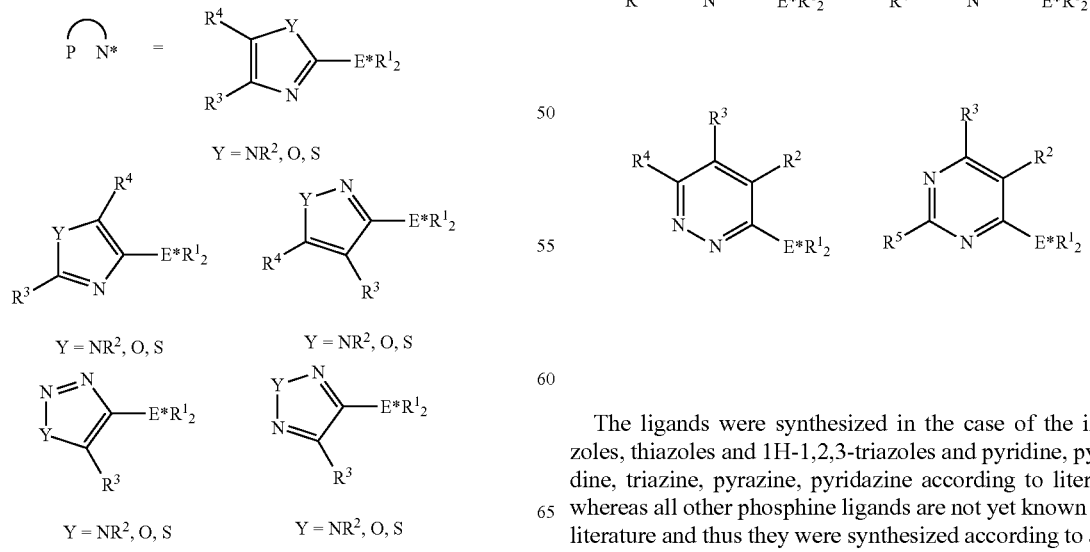

The ligands were synthesized in the case of the imidazoles, thiazoles and 1H-1,2,3-triazoles and pyridine, pyrimidine, triazine, pyrazine, pyridazine according to literature, whereas all other phosphine ligands are not yet known in the literature and thus they were synthesized according to a new synthesis method.

General Synthesis of the Phosphine Ligands

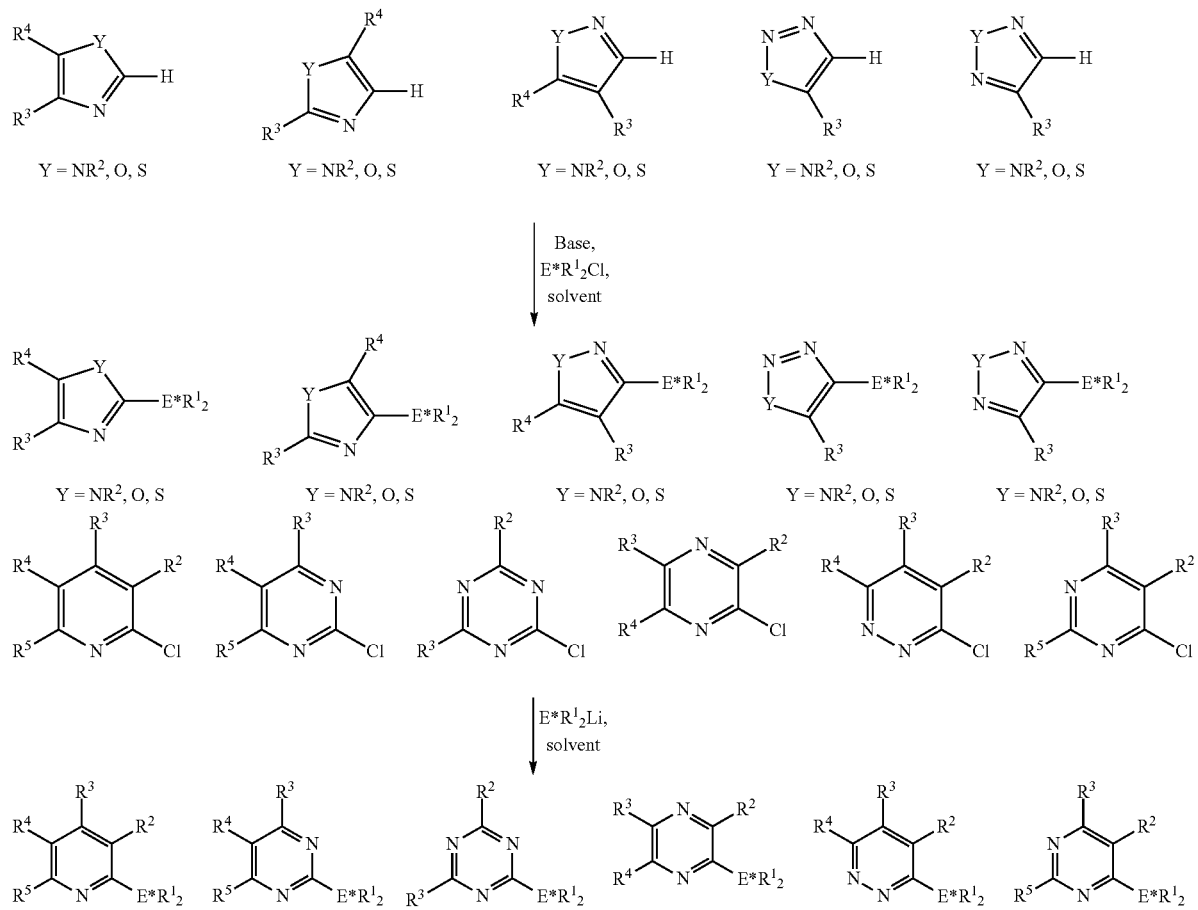

The identities of the ligands were unequivocally determined by NMR spectroscopy and mass spectroscopy.

Examples for Complexes of the form $Cu_4X^*_4(P\cap N^*)_2$

I. $P\cap N^*$=$Ph_2P$benzimidazole, 1a-e; $Cu_4I_4$($Ph_2P$benzimidazole)$_2$, 2a-e

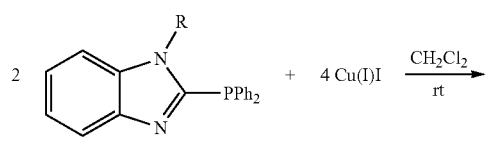

R = Me 1a,
Isopropyl 1b,
Hexyl 1c,
Ph 1d,
Bn 1e

-continued

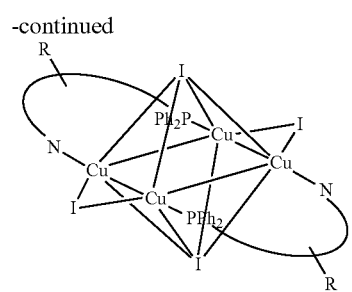

R = Me 2a,
Isopropyl 2b,
Hexyl 2c,
Ph 2d,
Bn 2e

The compounds 2a-e are white, fine-crystalline solids.

Characterization:

Elementary Analysis:

| 2a (R = Me) | calc.: C 34.45; H 2.46; N 4.02 |
| | found: C 34.23; H 2.42; N 3.85 |

-continued

| | |
|---|---|
| 2b (R = Isopropyl) | calc.: C 34.10; H 2.86; N 3.46 (x1 CH$_2$Cl$_2$) |
| | found: C 34.34; H 2.85; N 3.41 |
| 2c (R = Hexyl) | calc.: C 37.82; H 3.48; N 3.46 (x1 CH$_2$Cl$_2$) |
| | found: C 37.99; H 3.43; N 3.31 |
| 2d (R = Ph) | calc.: C 37.58; H 2.51; N 3.40 (x1.5 CH$_2$Cl$_2$) |
| | found: C 37.56; H 2.51; N 3.25 |

The crystal structures of 2b, 2c, 2e are shown in FIG. 1-3.

The emission spectra of 2a-c, 2e are shown in FIG. 4-7.

II. P∩N*=Ph$_2$PMe$_2$benzimidazole, 3a-e: Cu$_4$I$_4$(Ph$_2$PMe$_2$benzimidazole)$_2$, 4a-e

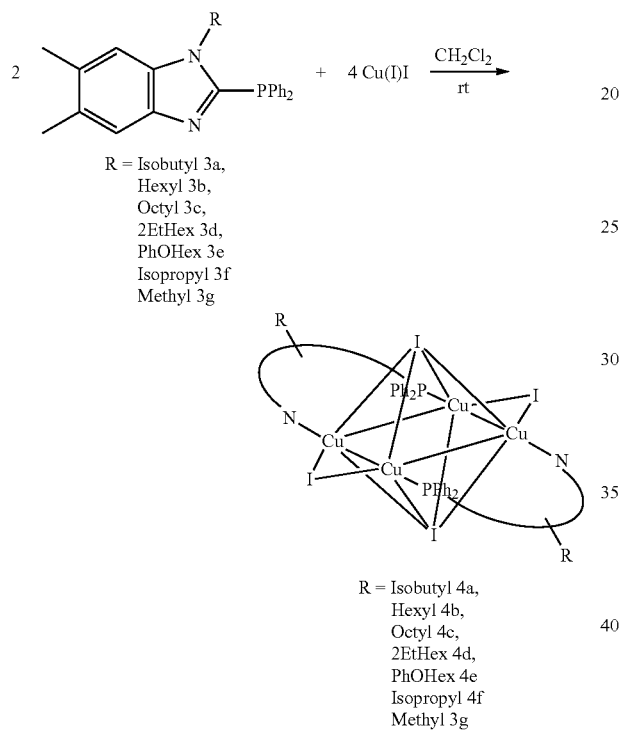

R = Isobutyl 4a,
Hexyl 4b,
Octyl 4c,
2EtHex 4d,
PhOHex 4e
Isopropyl 4f
Methyl 3g The compounds 4a-g are white, fine-crystalline solids.

Characterization:

Elementary Analysis:

| | |
|---|---|
| 4a (R = Isobutyl) | calc.: C 37.82; H 3.48; N 3.46 (x1 CH$_2$Cl$_2$) |
| | found: C 37.54; H 3.52; N 3.44 |
| 4b (R = Hexyl) | calc.: C 40.77; H 3.93; N 3.52 |
| | found: C 41.07; H 3.97; N 3.31 |
| 4d (R = 2EtHex) | calc.: C 42.30; H 4.28; N 3.40 |
| | found: C 42.37; H 4.23; N 3.30 |
| 4e (R = PhOHex) | calc.: C 44.66; H 3.97; N 3.16 |
| | found: C 44.60; H 3.96; N 2.92 |
| 4f (R = Isopropyl) | calc.: C 35.82; H 3.25; N 3.34 (x2 CH$_2$Cl$_2$) |
| | found: C 36.22; H 3.13; N 3.49 |
| 4g (R = Methyl) | calc.: C 35.20; H 2.89; N 3.65 (x1 CH$_2$Cl$_2$) |
| | found: C 35.28; H 2.77; N 3.67 |

The crystal structures of 4c, 4d, 4e are shown in FIG. 8-10.

The emission spectra of 4a, 4c, 4d, 4f, 4g are shown in FIG. 11-15.

III. P∩N*=Ph$_2$Phenimidazole, 5a-d: Cu$_4$I$_4$(Ph$_2$Phenimidazole)$_2$, 6a-d

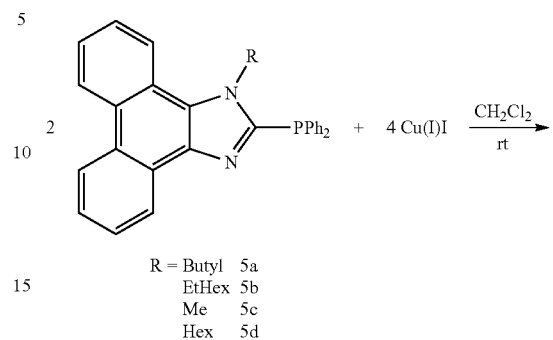

R = Butyl 5a
EtHex 5b
Me 5c
Hex 5d

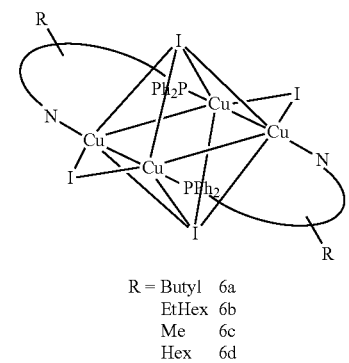

R = Butyl 6a
EtHex 6b
Me 6c
Hex 6d

The compounds 6a-d are white, fine-crystalline solids.

Characterization:

Elementary Analysis:

| | |
|---|---|
| 6a (R = Butyl) | calc.: C 41.58; H 3.16; N 3.03 (x2 CH$_2$Cl$_2$) |
| | found: C 41.34; H 3.17; N 2.76 |
| 6b (R = 2EtHexl) | calc.: C 46.94; H 3.94; N 3.13) |
| | found: C 47.02; H 3.91; N 3.02 |
| 6c (R = Me) | calc.: C 40.76; H 2.64; N 3.34 (x1 CH$_2$Cl$_2$) |
| | found: C 40.64; H 2.45; N 3.51 |
| 6d (R = Hex) | calc.: C 45.69; H 3.60; N 3.23 (x2 CH$_2$Cl$_2$) |
| | found: C 45.54; H 3.49; N 3.08 |

The crystal structure of 6a is shown in FIG. 16.

The emission spectra of 6a-d are shown in FIG. 17-20.

IV. P∩N*=Ph$_2$PImidazole. 7a-c: Cu$_4$I$_4$(Ph$_2$PImidazole)$_2$, 8a-c

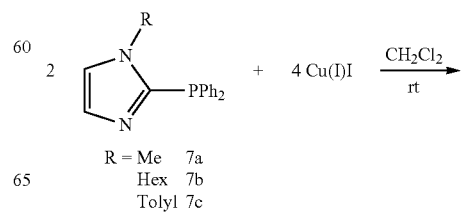

R = Me 7a
Hex 7b
Tolyl 7c

-continued

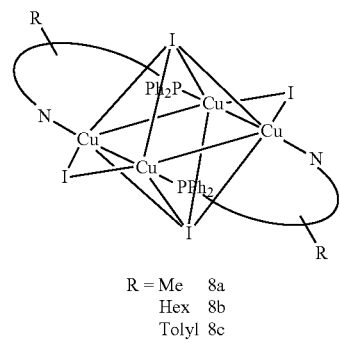

R = Me   8a
    Hex  8b
    Tolyl 8c

The compounds 8a-c are white, fine-crystalline solids.
Characterization:
Elementary Analysis:

| 8a (R = Me)    | calc.: C 28.74; H 2.34; N 4.06 (x1 CH$_2$Cl$_2$) |
|                | found: C 28.76; H 2.31; N 4.10 |
| 8b (R = Pent)  | calc.: C 33.57; H 3.27; N 3.87 (x1/2 CH$_2$Cl$_2$) |
|                | found: C 33.51, H 3.18; N 3.80 |
| 8c (R = Tolyl) | calc.: C 35.89; H 2.64; N 3.76 (x1/2 CH$_2$Cl$_2$) |
|                | found: C 35.78; H 2.58; N 3.60 |

The emission spectra of 8a-c are shown in FIG. 21-23.

V. P∩N*=Ph$_2$PBenzoxazole, 9a: Cu$_4$I$_4$(Ph$_2$PBenzoxazole)$_2$, 10a

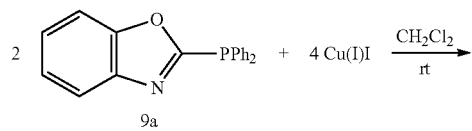

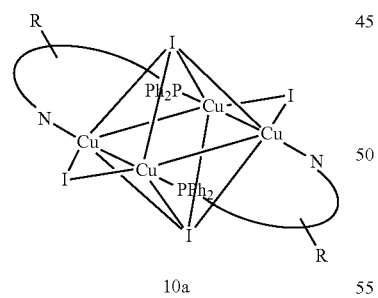

10a

The compound 10a is a white, fine-crystalline solid.
Characterization:
Elementary Analysis:

| 10a | calc.: C 33.35; H 2.06; N 2.05 |
|     | found: C 33.21; H 2.09; N 1.79 |

The emission spectrum of 10a is shown in FIG. 24.

VI. P∩N*=Ph$_2$PPh$_2$triazole, 11a: Cu$_4$I$_4$(Ph$_2$PPh$_2$triazole)$_2$, 12a

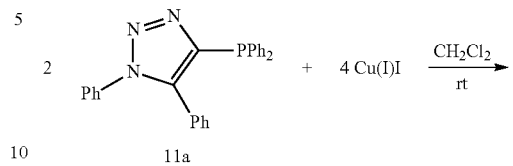

11a

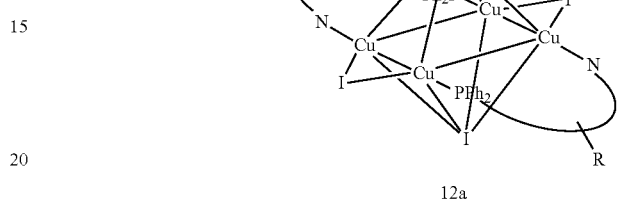

12a

The compound 12a is a white, fine-crystalline solid.
Characterization:
The crystal structure of 12a is shown in FIG. 25.

VII. P∩N*=Ph$_2$P-1,2,4-Triazole, 13a-e: Cu$_4$I$_4$(Ph$_2$P-1,2,4-Triazole)$_2$, 14a-e

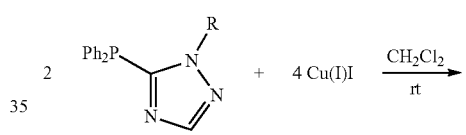

R = iPr        13a
    Tolyl      13b
    Hexyl      13c
    Ethylhexyl 13d
    Bn         13e

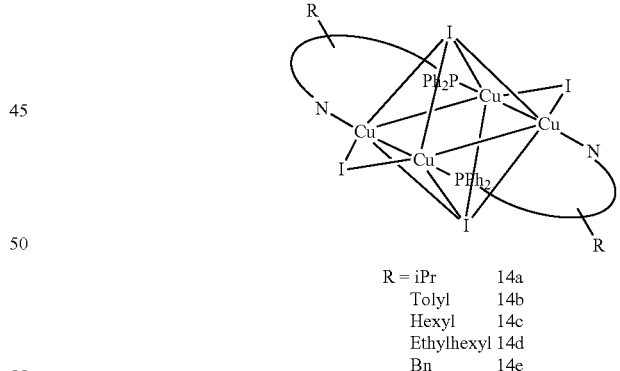

R = iPr        14a
    Tolyl      14b
    Hexyl      14c
    Ethylhexyl 14d
    Bn         14e The compounds 14a-e are white, fine-crystalline solids,
Characterization:
Elementary Analysis:

| 14a (R = iPr)   | calc.: C 31.12; H 2.97; N 6.05 (x1/2 Et$_2$O) |
|                 | found: C 31.02; H 2.83; N 6.16 |
| 14b (R = Tolyl) | calc.: C 34.24; H 2.50; N 5.46 (x1/2 CH$_2$Cl$_2$) |
|                 | found: C 34.36; H 2.45; N 5.61 |

| | |
|---|---|
| 14c (R = Pent) | calc.: C 32.40; H 3.15; N 5.97 |
| | found: C 32.79; H 3.11; N 5.94 |
| 14d (R = 2EtHex) | calc.: C 35.40; H 3.78; N 5.44 |
| | found: C 35.15; H 3.70; N 5.52 |
| 14e (R = Bn) | calc.: C 34.83; H 2.51; N 5.80 |
| | found: C 35.17; H 2.43; N 5.77 |

The emission spectra of 14a-e are shown in FIG. 26-30.

VIII. P∩N*=Ph2PPh$_2$Oxazole, 15a: Cu$_4$I$_4$(Ph2PPh$_2$Oxazole)$_2$, 16a

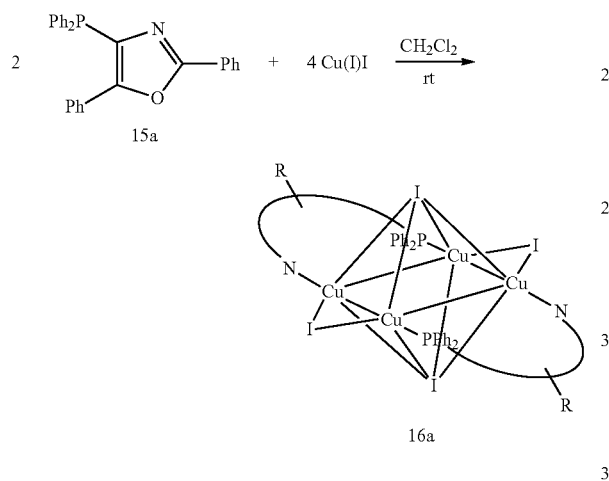

16a

The compound 16a is a white, fine-crystalline solid.

Characterization:
Elementary Analysis:

| | |
|---|---|
| 16a | calc.: C 39.85; H 2.55; N 1.69 (x1 CH$_2$Cl$_2$) |
| | found: C 40.04; H 2.43; N 1.40 |

IX. P∩N*=Ph$_2$PThiazole, 17a: Cu$_4$I$_4$(Ph$_2$PThiazole)$_2$, 18a

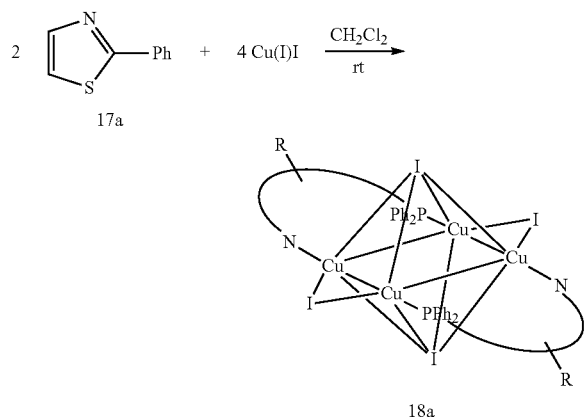

The compound 18a is a white, fine-crystalline solid.

Characterization:
Elementary Analysis:

| | |
|---|---|
| 18a | calc.: C 27.28; H 1.88; N 2.09; S 4.78 (x1/2 CH$_2$Cl$_2$) |
| | found: C 26.80; H 1.96; N 1.73; S 4.60 |

The emission spectrum of 18a is shown in FIG. 31.

X. P∩N*=Ph$_2$PPyridine, 19a-g: Cu$_4$I$_4$(Ph$_2$PPyridine)$_2$, 20a-g

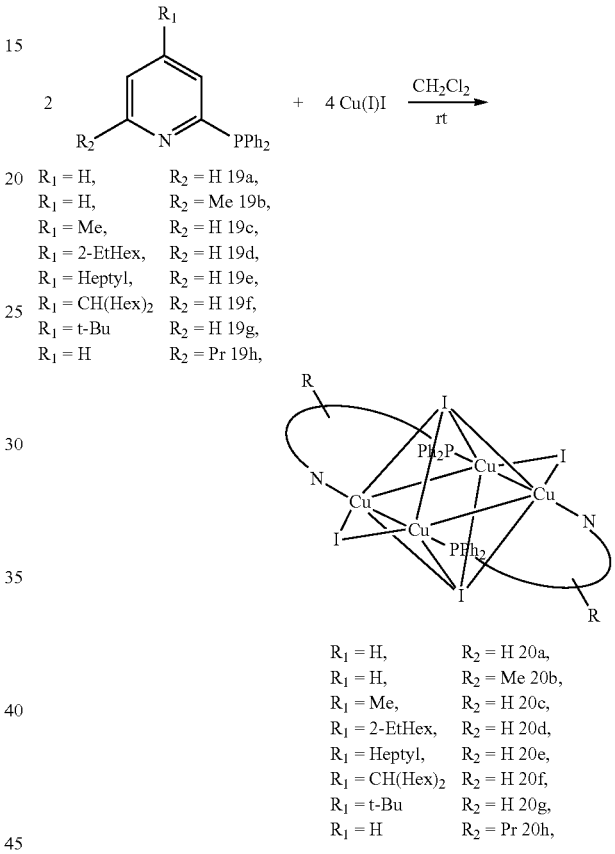

| | |
|---|---|
| R$_1$ = H, | R$_2$ = H 19a, |
| R$_1$ = H, | R$_2$ = Me 19b, |
| R$_1$ = Me, | R$_2$ = H 19c, |
| R$_1$ = 2-EtHex, | R$_2$ = H 19d, |
| R$_1$ = Heptyl, | R$_2$ = H 19e, |
| R$_1$ = CH(Hex)$_2$ | R$_2$ = H 19f, |
| R$_1$ = t-Bu | R$_2$ = H 19g, |
| R$_1$ = H | R$_2$ = Pr 19h, |

| | |
|---|---|
| R$_1$ = H, | R$_2$ = H 20a, |
| R$_1$ = H, | R$_2$ = Me 20b, |
| R$_1$ = Me, | R$_2$ = H 20c, |
| R$_1$ = 2-EtHex, | R$_2$ = H 20d, |
| R$_1$ = Heptyl, | R$_2$ = H 20e, |
| R$_1$ = CH(Hex)$_2$ | R$_2$ = H 20f, |
| R$_1$ = t-Bu | R$_2$ = H 20g, |
| R$_1$ = H | R$_2$ = Pr 20h, |

The compounds 20a-h are yellowish, fine-crystalline solids.

Characterization:
Elementary Analysis:

| | |
|---|---|
| 20a (R$_1$ = H; R$_2$ = H) | calc.: C 31.14; H 2.20; N 2.10 (x1/2 CH$_2$Cl$_2$) |
| | found: C 31.14; H 2.21; N 1.97 |
| 20b (R$_1$ = H; R$_2$ = Me) | calc.: C 32.85; H 2.45; N 2.13 |
| | found: C 32.49; H 2.38; N 1.88 |
| 20c (R$_1$ = Me; R$_2$ = H) | calc.: C 32.85; H 2.45; N 2.13 |
| | found: C 32.73; H 2.38; N 1.87 |
| 20d (R$_1$ = 2-EtHex; R$_2$ = H) | calc.: C 40.53; H 4.19; N 1.82 |
| | found: C 40.38; H 4.18; N 1.55 |
| 20e (R$_1$ = Heptyl; R$_2$ = H) | calc.: C 38.83; H 3.80; N 1.89 |
| | found: C 38.80; H 3.85; N 1.58 |
| 20f (R$_1$ = t-Bu; R$_2$ = H) | calc.: C 34.77; H 3.12; N 1.89 (x1 CH$_2$Cl$_2$) |
| | found: C 34.62; H 3.12; N 1.89 |
| 20g (R$_1$ = H; R$_2$ = Pr) | calc.: C 36.48; H 3.35; N 1.98 (x1/2 n-Hexan) |
| | found: C 36.55; H 3.10; N 1.83 |

The crystal structure of 20e is shown in FIG. 32.
The emission spectra of 20a-g are shown in FIG. 33-39.

XI. P∩N*=Ph₂PPyrimidine, 21a: Cu₄I₄(Ph₂PPyrimidine)₂, 22a

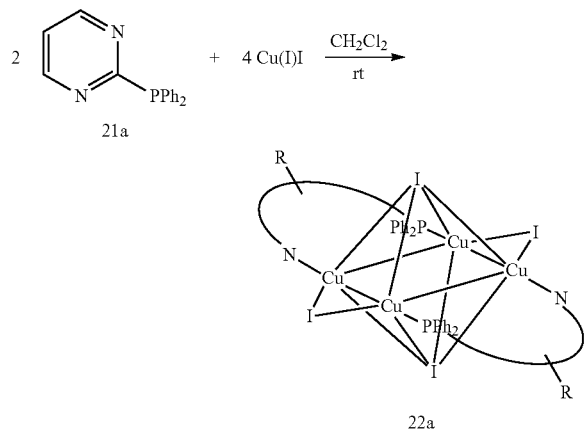

The compound 22a is a yellowish, fine-crystalline solid.
Characterization:
Elementary Analysis:

| 22a | calc.: C 29.79; H 2.03; N 4.34 |
|---|---|
|  | found: C 29.81; H 1.95; N 4.26 |

The emission spectra of 22a are shown in FIG. 40.

Although illustrative embodiments of the present invention have been described herein with reference to the accompying drawings, it is to be understood that the invention is not limited to those precise embodiments, and that various other changes and modifications may be made by one skilled in the art without departing from the scope or spirit of the invention.

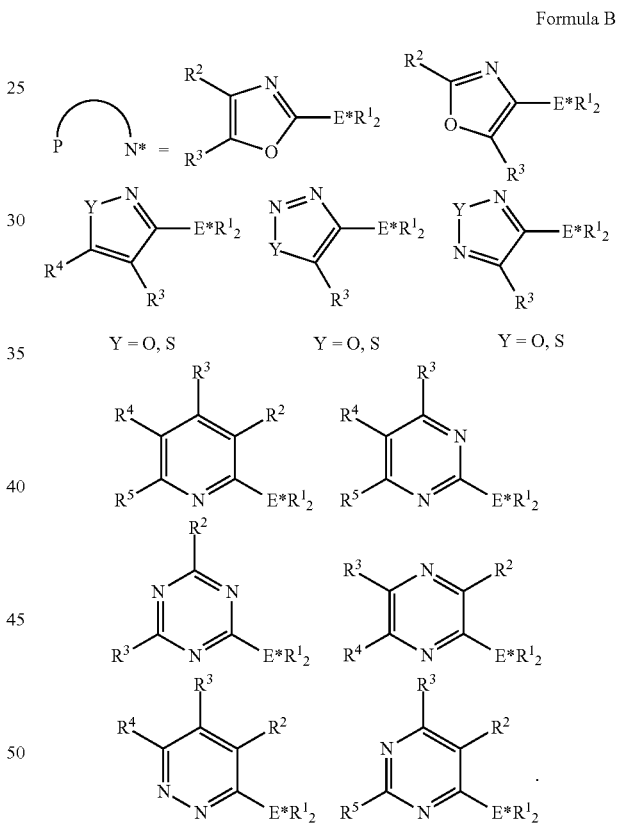

The invention claimed is:

1. A copper(I) complex of formula A

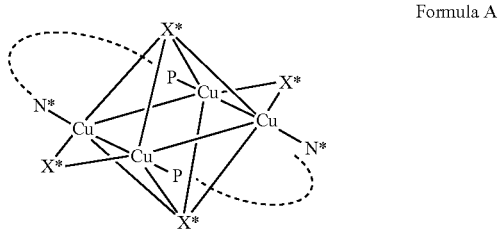

Formula A wherein:
X*=at least one of Cl, Br, I, CN and SCN
N*∩E=a bidentate ligand, wherein
E=phosphanyl/arsenyl group of the R₂E form, wherein R=one of alkyl, aryl, alkoxyl, phenoxyl, and amide;
N*=an imine function, which is part of a N-heteroaromatic 5-membered ring, which is selected from the group consisting of oxazole, imidazole, thiazole, isoxazole, isothiazole, pyrazole, 1,2,3-triazole, 1,2,3-oxadiazole, 1,2,5-oxadiazole, 1,2,3-thiadiazole and 1,2,5-thiadiazole, or an imine function, which is part of a N-heteroaromatic 6-membered ring, which is chosen from the group consisting of pyridine, pyrimidine, triazine, pyrazine and pyridazine; and ∩=at least one carbon atom, which is part of the aromatic group, wherein the at least one carbon atom is directly adjacent to both the imine nitrogen atom and to the phosphorous or arsenic atom.

2. The copper(I) complex according to claim 1, wherein N*∩E includes at least one substituent for increasing the solubility of the copper(I) complex in an organic solvent.

3. A copper(I) complex according to claim 2, wherein the substituent for increasing solubility is selected from the group consisting of:
   branched, unbranched or cyclic long-chained alkyl chains with a length of C1 to C30;
   branched, unbranched or cyclic long-chained alkoxy chains with a length of C1 to C30;
   branched, unbranched or cyclic long-chained perfluoro alkyl chains with a length of C1 to C30; and
   short-chained polyethers with a chain length of 3-50 repeating units.

4. The copper(I) complex according to claim 1, wherein N*∩E is selected from the group consisting of:

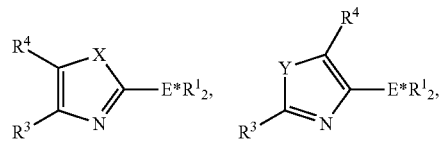

X = NR²: 1R²-2E*R¹₂-4R³-5R⁴-1H-Imidazole
X = O: 2E*R¹₂-4R³-5R⁴-Oxazole
X = S: 2E*R¹₂-4R³-5R⁴-Thiazole Y = NR²: 1R²-4E*R¹₂-2R³-5R⁴-1H-Imidazole
Y = O: 4E*R¹₂-2R³-5R⁴-Oxazole
Y = S: 4E*R¹₂-2R³-5R⁴-Thiazole

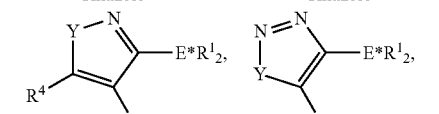

Y = NR²: 1R²-3E*R¹₂-4R³-5R⁴-1H-Pyrazole
Y = O: 3E*R¹₂-4R³-5R⁴-Isoxazole
Y = S: 3E*R¹₂-4R³-5R⁴-Isothiazole Y = NR²: 1R²-4E*R¹₂-5R³-1H-1,2,3-Trizole
Y = O: 4E*R¹₂-5R³-1,2,3-Oxadiazole
Y = S: 4E*R¹₂-5R³-1,2,3-Thiadiazole

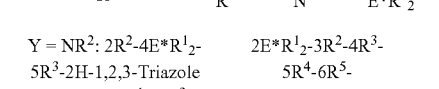

Y = NR²: 2R²-4E*R¹₂-5R³-2H-1,2,3-Triazole
Y = O: 3E*R¹₂-4R³-1,2,5-Oxadiazole
Y = S: 3E*R¹₂-4R³-1,2,5-Thiadiazole 2E*R¹₂-3R²-4R³-5R⁴-6R⁵-Pyridine

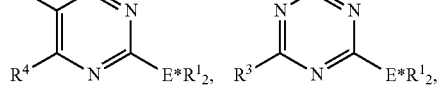

2E*R¹₂-4R²-5R³-6R⁴-Pyrimidine

2E*R¹₂-4R²-6R³-1,3,5-Triazine

-continued

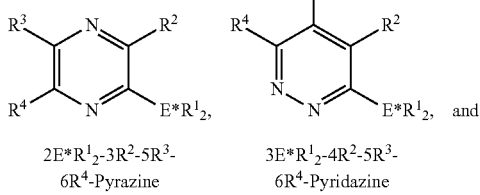

2E*R¹₂-3R²-5R³-
6R⁴-Pyrazine

3E*R¹₂-4R²-5R³-
6R⁴-Pyridazine, and

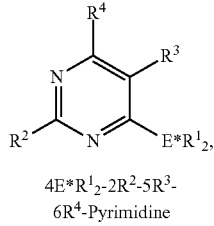

4E*R¹₂-2R²-5R³-
6R⁴-Pyrimidine wherein
X=O or NR²
Y=O, NR² or S
E*=As or P
R1-R5 are each independently from each other hydrogen, a halogen or substituents which are bound via oxygen (—OR), nitrogen (—NR₂) or silicon atoms (—SiR₃), as well as alkyl-, aryl-, heteroaryl-, alkenyl-, alkinyl- groups and respectively substituted alkyl-, aryl-, heteroaryl- and alkenyl-groups.

5. A method for preparing the copper(I) complex of claim 1, comprising:
performing a reaction of N*∩E with Cu(I)X*.

6. The method according to claim 5, wherein the reaction is performed in dichloromethane.

7. The method according to claim 6, further comprising adding diethyl ether or pentane to obtain the copper(I) complex in the form of a solid.

8. The method according to claim 5, further comprising substituting at least one ligand N*∩E with at least one substituent selected from the group consisting of:
long-chained branched, unbranched or cyclic alkyl chains with a length of C1 to C30;
long-chained branched, unbranched or cyclic alkoxy chains with a length of C1 to C30;
branched, unbranched or cyclic perfluoro alkyl chains with a length of C1 to C30; and
short-chained polyethers.

9. The method according to claim 5, further comprising preparing the bidentate ligand having the formula B, Formula B

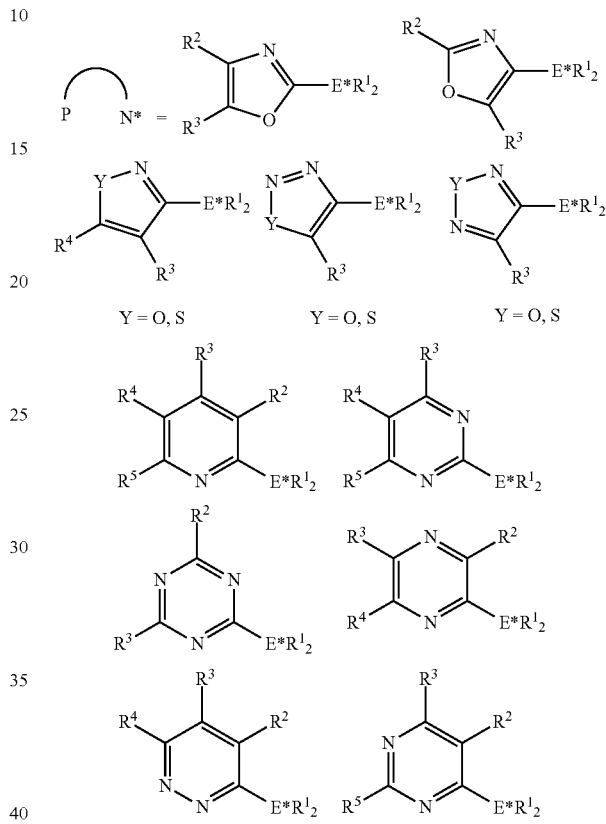

pursuant to one of:
a)

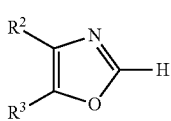 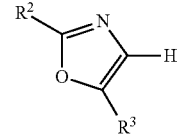 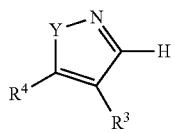 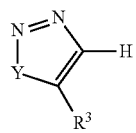 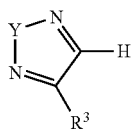

Y = O, S     Y = O, S     Y = O, S

↓ Base, E*R¹₂Cl, solvent

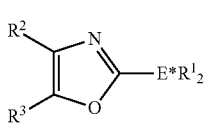 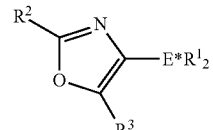 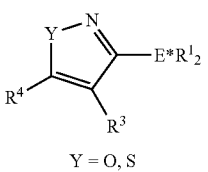 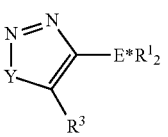 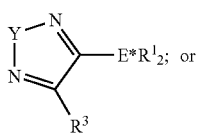

Y = O, S     Y = O, S     Y = O, S or b)

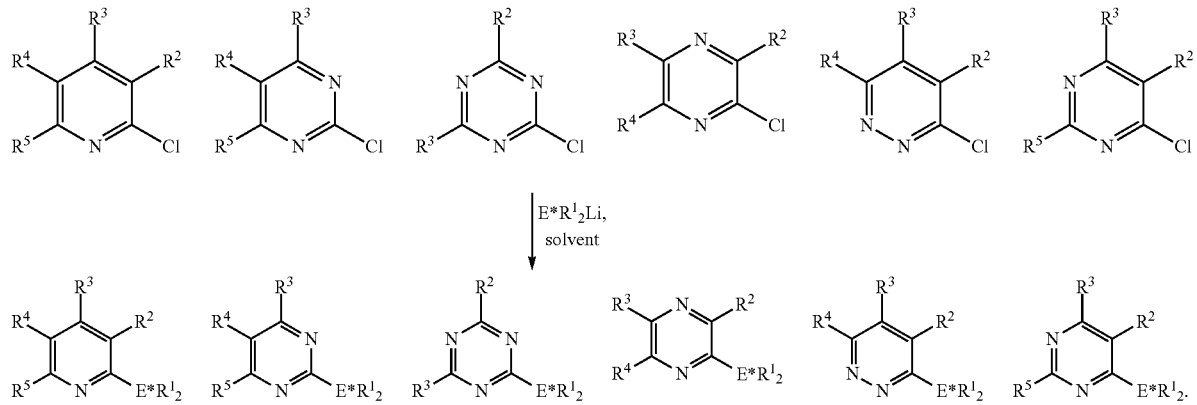

10. An optoelectronic component comprising at least one of an emitter and an absorber having the copper(I) complex of claim 1.

11. The optoelectronic component according to claim 10, wherein the optoelectronic component is selected from the group consisting of:
an organic light emitting diode (OLED);
a light emitting electrochemical cell;
an OLED-sensor;
an organic solar cell;
an organic field-effect transistor;
an organic laser; and
a down conversion element.

12. An optoelectronic component comprising the copper (I) complex of claim 1.

13. The optoelectronic component according to claim 12, wherein the optoelectronic component is selected from the group consisting of an organic light emitting component, an organic diode, an organic solar cell, an organic transistor, an organic light emitting diode, a light emitting electrochemical cell, an organic field-effect transistor and an organic laser.

14. A method for manufacturing an optoelectronic component, comprising applying the copper(I) complex of claim 1 onto a carrier.

15. The method according to claim 14, wherein the application of the copper(I) complex is performed by a wet-chemical process, by using a colloidal suspension means or by sublimation.

16. The cooper(I) complex according to claim 1, wherein the bidentate ligand has the formula B, Formula B